United States Patent [19]

Kada et al.

[11] Patent Number: 5,543,912
[45] Date of Patent: Aug. 6, 1996

[54] REFLECTOMETRY OF AN OPTICAL WAVEGUIDE USING A LOW COHERENCE REFLECTOMETER

[75] Inventors: Kazumasa Kada, Mito; Masaharu Horigichi, Naka-gun; Hiroaki Yamada, Katsuta, all of Japan

[73] Assignee: Nippon Telegraph and Telephone Corporation, Tokyo, Japan

[21] Appl. No.: 237,483

[22] Filed: May 3, 1994

[30] Foreign Application Priority Data

May 7, 1993 [JP] Japan ................................ 5-106381
Mar. 9, 1994 [JP] Japan ................................ 6-038127

[51] Int. Cl.$^6$ .................. G01N 21/84; G01N 21/88; H01S 3/02
[52] U.S. Cl. .................. 356/73.1; 359/341; 359/347
[58] Field of Search .................. 356/73.1; 359/333, 359/341, 347

[56] References Cited

FOREIGN PATENT DOCUMENTS 63-204130   8/1988   Japan .
63-196829   8/1988   Japan .
5-126673    5/1993   Japan .

OTHER PUBLICATIONS

Ultrahigh–Sensitivity Low Coherence OTDR Using $Er^{3+}$–Doped High–Power Superfluorescent Fibre Source, Electronics Letters 2nd Jan. 1992, vol. 28, No. 1, pp. 29–30.
Low Coherence Reflectometry Using Wavelength–Tunable Super–fluorescent Fibre Source, Electronics Letters 8th Jul. 1993, vol. 29, No. 14, pp. 1273–1274.
Jagged Apperance of Rayleigh–Backscatter Signal in Ultrahigh–Resolution Optical Time–Domain Reflectometry Based on Low–Coherence Interference, 1991 Optical Society of America, Optics Letters, vol. 16, No. 18, Sep. 15, 1991, pp. 1433–1435.
Proceedings of the 1993 IEICE Fall Conference, Sep. 5–8, 1993, Sapporo, Hokkaido Institute of Technology, The Institute of Electronics, Information and Communication Engineers, pp. 4–352 Speckle–Noise Reduction in Optical Low Coherence Reflectometry C–272.
Low Coherence Reflectometry Using Automatically–Wavelength–Turnable Fibre Source, C–417, pp. 4–414, Kazumasa Takada, Hiroaki Yamada, Masaharu Horiguchi, NTT Opto––electronics Laboratories, 1994.

*Primary Examiner*—Vincent P. McGraw
*Attorney, Agent, or Firm*—Kenyon & Kenyon

[57] ABSTRACT

A reflectomerry method and device are disclosed for measuring the loss distribution of an optical waveguide on the basis of Rayleigh back-scattered signals from an optical waveguide under test. Light output from a tunable low-coherent. light source, in which laser oscillation is suppressed, is divided into first and second lights. Local oscillator light is generated by propagating the first light over a variable optical path length determined by a movable mirror. The second light is used as a probe light which is launched into the optical waveguide under test. The local oscillator light is combined with light reflected from the waveguide under test. An average value of the Rayleigh back-scattered signals from the waveguide under test is obtained at respective center wavelengths of the light source by measuring the intensity of the combined light while maintaining the variable optical path length constant and varying the center wavelength of the light source. The average value of the Rayleigh back-scattered signals is thus obtained at a point of the waveguide under test. After changing the variable optical path length by incrementally shifting the movable mirror, the above procedure is repeated to obtain an average value of the Rayleigh back-scattered signals at successive points of the waveguide under test. By thus reducing the number of times the mirror needs to be shifted, the time required for measuring the entire waveguide is reduced.

20 Claims, 18 Drawing Sheets

5,543,912

REFLECTOMETRY OF AN OPTICAL WAVEGUIDE USING A LOW COHERENCE REFLECTOMETER

BACKGROUND OF THE INVENTION

1. Field of the Invention

The present invention relates to a reflectometry and a reflectometer which measure the loss distribution of an optical waveguide on the basis of Rayleigh back-scattering profile, and more particularly to a method and apparatus implementing spatial resolution of a millimeter region by using a so-called optical low coherence reflectometer utilizing optical low coherence interference.

2. Description of Related Art

FIG. 1 shows a typical return waveform obtained by measuring Rayleigh back-scattering from a 70 km long optical fiber cable by an OTDR (Optical Time Domain Reflectometer). The attenuation of the signal along the length of the optical fiber gives an attenuation coefficient (dB/km) of the optical fiber, and the amount of a stepwise attenuation of the signal gives splice loss at a splice point. The OTDR, however, cannot be used for measuring a waveguide, because its length is several meters at most. Instead, a so-called optical low coherence reflectometer is used which utilizes the interference of low-coherent light.

FIG. 2 shows a basic setup of a conventional optical low coherence reflectometer (OLCR). In this figure, the reference numeral 1 designates a low-coherent light source, which suppresses laser oscillation to emit low-coherent light whose spectral width is, for example, 20 nm. The reference numeral 2 designates an optical fiber coupler, 3 and 4 designate branch ports of the coupler 2, 5 designates a collimator lens, 6 designates a mirror, 7 designates a waveguide under test, 8 designates an output port of the coupler 2, 9 designates a photodetector, and 10 designates a selective level meter.

The emitted light from the light source 1 is divided into two parts by the coupler 2. The first part is passed through the port 3, collimated by the collimator lens 5, reflected by the mirror 6, and incident onto the coupler 2 again, so that the light propagating the output port 8 is used as local oscillator light. The other part is passed through the port 4, and incident onto the waveguide 7 under test. Back-scattered light, which is produced by Rayleigh back-scattering throughout the length of the waveguide 7 under test, travels through the port 4, and is combined with the local oscillator light. The combined light is received by the photodetector 9, and the interference intensity is measured by the selective level meter 10.

When performing measurement by the setup, the mirror 6 is shifted step by step by a very small amount, and the interference intensity for respective positions of the mirror 6 is detected by the selective level meter 10. Since the coherent length of the light source 1 is approximately 20 μm, the reflected light (reverse scattered light) interferes with the local oscillator light only when the optical path length difference between the reflected light and the local oscillator light is within 20 μm. Accordingly, each position of the mirror 6 can be considered to have a one-to-one correspondence with each one of the back-scattering positions along the waveguide 7, and the interference intensity measured at each point is proportional to the reflection intensity. This is the principle of the conventional setup, which makes it possible to measure the back-scattering from the waveguide 7 by shifting the mirror 6.

FIG. 3 shows a setup of the low-coherent light source 1 using an erbium-doped optical fiber. In this figure, the reference numeral 11 designates a pump source module whose emission wavelength is 1.48 μm. The reference numeral 12 designates a WDM (Wavelength-Division Multiplexer) coupler, 13 designates an erbium-doped optical fiber, 14 designates a mirror, and 15 designates an optical isolator which is incorporated to suppress reflection. The light emitted from the pump source module 11 enters the erbium-doped optical fiber 13. Then, the optical fiber 13 emits superfluorescent light whose center wavelength is about 1550 nm and whose spectral width is 20 nm by launching the pump light into the fiber. The superfluorescent light is reflected by the mirror 14, and is incident onto the optical fiber 13, again. The incident light is amplified by the optical fiber 13, propagates straight through the WDM coupler 12, and passes through the optical isolator 15. This setup makes it possible to suppress the laser oscillation by the optical isolator 15, and to emit the amplified superfluorescent light, thereby implementing a low-coherent light source whose spectral width is 20 nm and whose optical output is 1 mW.

This type of an optical low coherence reflectometer measures the reflection power using the interference between the oscillator light and the reflected light. Since scattering particles are distributed throughout the waveguide 7 under test, the detection signal depends not only on the reflection intensity of the individual scattering particles but also on the optical path differences between scattering particles, that is, the phase differences between scattered light. Therefore, the Rayleigh scattering particles, whose distribution varies randomly along the length of the waveguide with correlation lengths of submicron order, cause speckle noise which varies randomly at a pitch of several tens of microns along the length of the wavelength as shown in FIG. 4.

In the experiment of FIG. 4, the mirror 6 of FIG. 2 was shifted 70 times at every 15 μm interval, and the reflection light from the waveguide 7 under test (a silica-based optical waveguide) was detected at each position of the mirror 6. This means that the waveguide 7 under test was detected at every 10 μm interval, because the refractive index of the waveguide 7 is 1.5, and hence, 15 μm/1.5=10 μm. Since the 700 μm long waveguide had little loss, it was expected that the detection signal had an approximately constant intensity over that length. Actually, however, a detection signal, which changed randomly as shown in FIG. 4, was observed.

One of the methods for obtaining loss information from the signal which changes randomly as in FIG. 4 is a smoothing method which averages the signal along the length of the waveguide. The smoothing method is described in K. Takada, et al. "Jagged appearance of Rayleigh back-scattered signal in ultrahigh-resolution optical time-domain reflectometry based on low-coherence interference", Optics Letters, Vol. 16, No. 18, pp. 1433–1435, Sep. 15, 1991.

This method will be explained more specifically referring to FIGS. 5, and 5A in which a 40 cm long silica-based waveguide is tested. In this method, the waveguide under test is divided into N=400 intervals in 1 mm increments, for example, and an averaged Rayleigh back-scattered signal is obtained in each interval. To perform this, the mirror 6 is shifted 100 times in 15 μm steps in each interval of 1 mm as shown in FIG. 5A, and the signal is detected at each position of the mirror. After completing the total of 100 measurements in an interval, the average of these signals is calculated. The average is adopted as the Rayleigh back-scattered signal of that interval. Thus, this measurement requires 100 times intermittent shifts of the mirror 6 and the detections of the reflected signals to obtain the average value at each interval. This means that 40,000 (=100×400) times of shifts of the mirror 6 and detections of the reflected signals are necessary to test the entire length of the 40 cm long waveguide 7 under test. In other words, the conventional method requires a great number of shifts of the mirror 6 and detections of the reflected signals in order to pick up the loss information of the waveguide. This arises a problem in that the measurement takes a long time, and mechanical abrasion of a translation stage, on which the mirror is mounted, due to the shift of the mirror is large.

In addition, since the mirror vibrates slightly after the 15 μm step shift is completed, the detection of the reflected signal should be carried out after the vibration falls. This requires approximately 0.1 second, and hence, the measurement at a particular position of the mirror requires at least 0.1 second, which in turn means that a minimum of 4,000 seconds (=0.1×40,000) is necessary to complete the test of the 40 cm long waveguide. Furthermore, to reduce the detection time to less than 0.1 second, the response time must be increased by widening the detection bandwidth. This causes a new problem in that the signal-to-noise ratio (S/N) of the detection is degraded and its sensitivity is reduced. In a common experiment, since the bandwidth of the detection is set at about 3 Hz to increase its sensitivity, the measurement takes about 1 second for each position.

SUMMARY OF THE INVENTION

It is therefore an object of the present invention to provide a reflectometry and a reflectometer which can reduce the number of shifts of the mirror, thereby reducing the time required for measurement.

In a first aspect of the present invention, there is provided a reflectometry comprising the steps of:

splitting output light from a light source into first light and second light, the light source being a low-coherent light source in which laser oscillation is suppressed, and the center wavelength of the light source being tunable;

generating local oscillator light by propagating the first light by a variable optical path length;

launching the second light into an optical waveguide under test as probe light;

combining the local oscillator light with reflected light from the optical waveguide under test to generate combined light;

obtaining an average value of Rayleigh back-scattered signals from the optical waveguide under test at respective center wavelengths of the light source by measuring the intensity of the combined light while maintaining the variable optical path length at a constant value and varying the center wavelength of the light source; and obtaining an average Rayleigh back-scattered quantity at each point of the optical waveguide under test by repeating the step of obtaining an average value of Rayleigh back-scattered signals, after changing the variable optical path length.

Here, the step of obtaining an average value of Rayleigh back-scattered signals may comprise the step of correcting the intensity of the Rayleigh back-scattered signals detected at each center wavelength of the light source by using optical output power of the light source at each center wavelength.

The step of obtaining an average value of Rayleigh back-scattered signals may comprise the step of generating a DC component of the Rayleigh back-scattered signals which vary in response to the center wavelength of the light source, when the center wavelength is swept at a fixed period.

The step of obtaining an average value of Rayleigh back-scattered signals may comprise the step of controlling the output power of the light source to take a substantially constant value.

In a second aspect of the present invention, there is provided a reflectometer comprising:

a light source generating low-coherent light by suppressing laser oscillation, the center wavelength of the low-coherent light being tunable;

means for splitting the output light from the light source into first light and second light;

means for generating local oscillator light by propagating the first light by a variable optical path length;

means for launching the second light into an optical waveguide under test as probe light;

means for combining the local oscillator light with reflected light from the optical waveguide under test to generate combined light;

detecting means for detecting the intensity of a Rayleigh back-scattered signal from the optical waveguide under test on the basis of the combined light; and output means for obtaining an average value of Rayleigh back-scattered signals from the optical waveguide under test at respective center wavelengths of the light source on the basis of the output of the means for detecting while maintaining the variable optical path length at a constant value and varying the center wavelength of the light source, wherein an average Rayleigh back-scattered quantity at each point of the optical waveguide under test is obtained by changing the variable optical path length.

Here, the output means may correct the intensity of each of the Rayleigh back-scattered signals in accordance with output power of the light source at each center wavelength, the each of the Rayleigh back-scattered signals being detected by the detecting means at each center wavelength of the light source.

The light source may comprise means for sweeping its center wavelength at a fixed period, and the output means may comprise means for generating a DC component of the Rayleigh back-scattered signals which vary in response to the center wavelength of the light source.

The light source may comprise means for controlling the output power of the light source to take a substantially constant value.

The detecting means may have a response speed slower than the fixed period over which the center wavelength of the light source is swept.

The output means may comprise a lowpass filter which lowpasses the output of the detecting means.

The light source may comprise:

an optical amplifier emitting superfluorescent light;

a first optical bandpass filter whose center wavelength of a passband is tunable, and whose first end is connected to a first end of the optical amplifier;

incident means, connected to a second end of the first optical bandpass filter, for feeding back the superfluorescent light emitted from the first end of the optical amplifier to the first end of the optical amplifier through the first optical bandpass filter;

an optical isolator whose first end is connected to a second end of the optical amplifier, the optical isolator preventing output light from the second end of the optical amplifier from being fed back to the optical amplifier;

a second optical bandpass filter whose center wavelength of the passband is tunable, and whose first end is connected to a second end of the optical isolator, and a wavelength control means for changing the center wavelength of the passband of the first optical bandpass filter and that of the second optical bandpass filter in such a manner that the two center wavelengths of the passband agree with each other, wherein output light of the light source being emitted from a second end of the second optical bandpass filter.

The light source may comprise:

a first optical amplifier emitting superfluorescent light;

a first optical bandpass filter whose center wavelength of the passband is tunable, and whose first end is connected to a first end of the first optical amplifier, the first optical bandpass filer bandpassing the superfluorescent light;

a second optical amplifier whose first end is connected to a second end of the first optical bandpass filter, and which amplifies a light signal emitted from the first optical bandpass filter;

a second optical bandpass filter whose center wavelength of the passband is tunable, and whose first end is connected to a second end of the second optical amplifier, the second optical bandpass filter bandpassing output light from the second optical amplifier;

a wavelength control means for changing the center wavelength of the passband of the first optical bandpass filter and that of the second optical bandpass filter in such a manner that the two center wavelengths of the passband agree with each other; and an optical isolator connected between the second optical amplifier and the first optical bandpass filter, or between the second optical amplifier and the second optical bandpass filter, wherein output light of the light source is emitted from a second end of the second optical bandpass filter.

A second end of the first optical amplifier may undergo a treatment for reducing the reflectivity of the second end.

The light source may comprise:

a four-port optical circulator having four ports a, b, c and d, a light signal propagating from the a port to the d port, from the b port to the c port, from the c port to the a port, and from the d port to the b port;

an optical amplifier whose ends are connected to the a port and b port of the four-port optical circulator, the optical amplifier emitting superfluorescent light;

an optical bandpass filter whose first end is connected to the c port of the four-port circulator; and a three-port optical circulator connected between a second end of the optical bandpass filter and the d port of the four-port optical circulator, the three-port optical circulator supplying the optical bandpass filter with emitted light from the d port of the four-port optical circulator, and emitting light outputted from the optical bandpass filer to the outside.

The light source may comprise:

a four-port optical circulator having four ports a, b, c and d, a light signal propagating from the b port to the c port, from the c port to the a port, and from the d port to the b port;

an optical amplifier whose ends are connected to the c port and d port of the four-port optical circulator, the optical amplifier emitting superfluorescent light;

an optical bandpass filter whose first end is connected to the b port of the four-port circulator; and a three-port optical circulator connected between a second end of the optical bandpass filter and the a port of the four-port optical circulator, the three-port optical circulator supplying the optical bandpass filter with emitted light from the a port of the four-port optical circulator, and emitting light outputted from the optical bandpass filer to the outside.

The light source may further comprise control means for controlling output power of the light source at a constant value.

In a third aspect of the present invention, there is provided a light source comprising:

an optical amplifier emitting superfluorescent light;

a first optical bandpass filter whose center wavelength of a passband is tunable, and whose first end is connected to a first end of the optical amplifier;

incident means, connected to a second end of the first optical bandpass filter, for feeding back the superfluorescent light emitted from the first end of the optical amplifier to the first end of the optical amplifier through the first optical bandpass filter;

an optical isolator whose first end is connected to a second end of the optical amplifier, the optical isolator preventing output light from the second end of the optical amplifier from being fed back to the optical amplifier;

a second optical bandpass filter whose center wavelength of the passband is tunable, and whose first end is connected to a second end of the optical isolator, and a wavelength control means for changing the center wavelength of the passband of the first optical bandpass filter and that of the second optical bandpass filter in such a manner that the two center wavelengths of the passband agree with each other, wherein output light of the light source being emitted from a second end of the second optical bandpass filter.

In a fourth aspect of the present invention, there is provided a light source comprising:

a first optical amplifier emitting superfluorescent light;

a first optical bandpass filter whose center wavelength of the passband is tunable, and whose first end is connected to a first end of the first optical amplifier, the first optical bandpass filer bandpassing the superfluorescent light;

a second optical amplifier whose first end is connected to a second end of the first optical bandpass filter, and which amplifies a light signal emitted from the first optical bandpass filter;

a second optical bandpass filter whose center wavelength of the passband is tunable, and whose first end is connected to a second end of the second optical amplifier, the second optical bandpass filter bandpassing output light from the second optical amplifier;

a wavelength control means for changing the center wavelength of the passband of the first optical bandpass filter and that of the second optical bandpass filter in such a manner that the two center wavelengths of the passband agree with each other; and an optical isolator connected between the second optical amplifier and the first optical bandpass filter, or between the second optical amplifier and the second optical bandpass filter, wherein output light of the light source is emitted from a second end of the second optical bandpass filter.

Here, a second end of the first optical amplifier may undergo a treatment for reducing the reflectivity of the second end.

In a fifth aspect of the present invention, there is provided a light source comprising:

a four-port optical circulator having four ports a, b, c and d, a light signal propagating from the a port to the d port, from the b port to the c port, from the c port to the a port, and from the d port to the b port;

an optical amplifier whose ends are connected to the a port and b port of the four-port optical circulator, the optical amplifier emitting superfluorescent light;

an optical bandpass filter whose first end is connected to the c port of the four-port circulator; and a three-port optical circulator connected between a second end of the optical bandpass filter and the d port of the four-port optical circulator, the three-port optical circulator supplying the optical bandpass filter with emitted light from the d port of the four-port optical circulator, and emitting light outputted from the optical bandpass filer to the outside.

In a sixth aspect of the present invention, there is provided a light source comprising:

a four-port optical circulator having four ports a, b, c and d, a light signal propagating from the b port to the c port, from the c port to the a port, and from the d port to the b port;

an optical amplifier whose ends are connected to the c port and d port of the four-port optical circulator, the optical amplifier emitting superfluorescent light;

an optical bandpass filter whose first end is connected to the b port of the four-port circulator; and a three-port optical circulator connected between a second end of the optical bandpass filter and the a port of the four-port optical circulator, the three-port optical circulator supplying the optical bandpass filter with emitted light from the a port of the four-port optical circulator, and emitting light outputted from the optical bandpass filer to the outside.

Here, the light source may further comprise control means for controlling output power of the light source at a constant value.

The above and other objects, effects, features and advantages of the present invention will become more apparent from the following description of the embodiments thereof taken in conjunction with the accompanying drawings.

DETAILED DESCRIPTION OF PREFERRED EMBODIMENTS

The invention will now be described with reference to the accompanying drawings. Before describing embodiments, however, the principle of the present invention will be described.

The present invention abandons the conventional smoothing method based on the shift and averaging, but performs wavelength averaging of Rayleigh back-scattered signals by changing center wavelength of the low-coherent light source of the reflectometer while keeping the mirror at a position corresponding to a measurement position in the waveguide under test, thereby obtaining the averaged Rayleigh back-scattered signal. This method will be described in more detail.

If the mirror is set at a particular position, the intensity $I(x)$ of a Rayleigh back-scattered signal at a measurement position x, which the optical low coherence reflectometer detects is given by the following equation.

$$I(x) = CP^2 \sum_{k,j} T(x_k)T(x_j)a_k a_j R(x_k - x)R(x_j - x) \times \cos[4\pi\sigma_0 n(x_k - x_j)] \quad (1)$$

Figure 6:
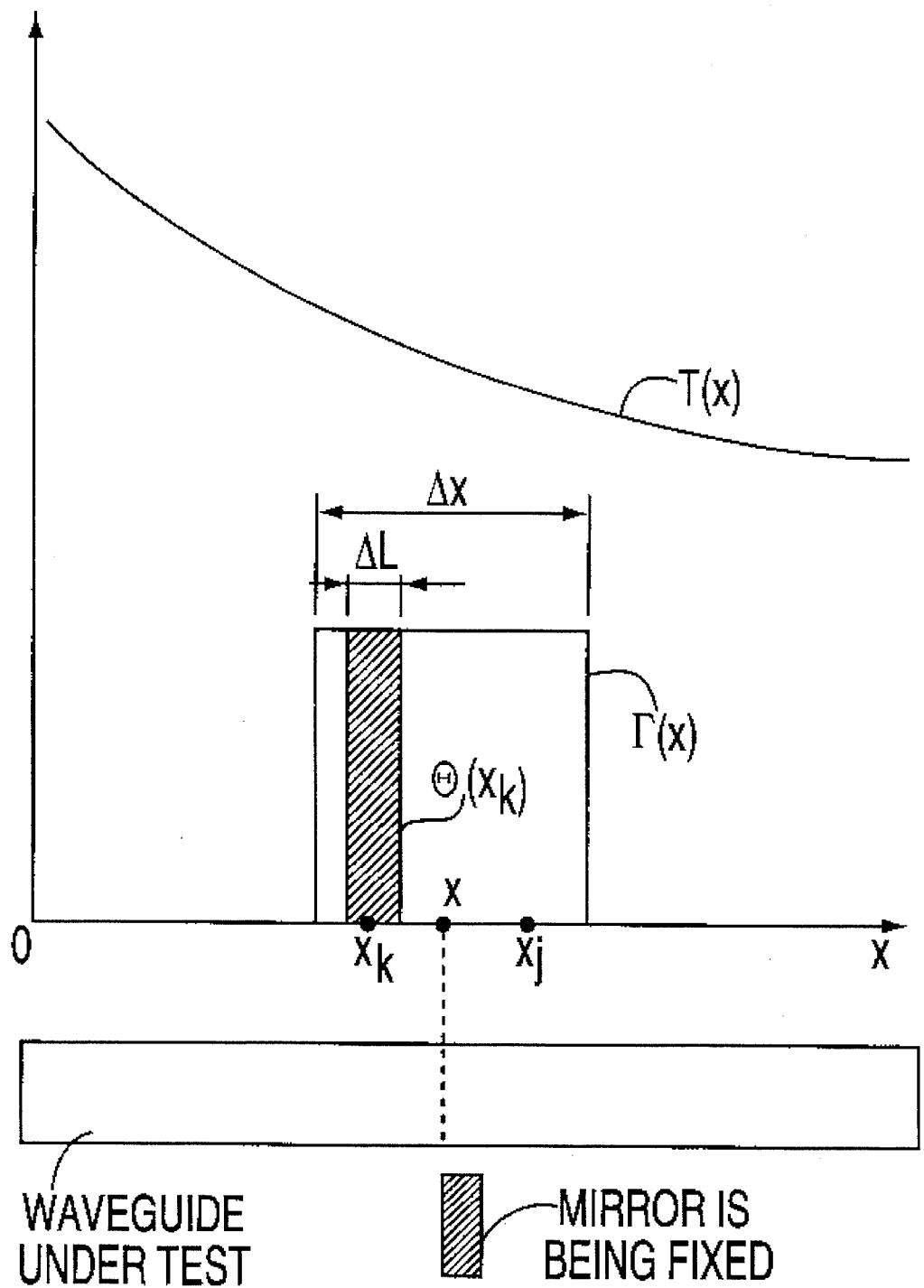
FIG. 6 is a diagram for explaining the principle of the present invention, which illustrates relationships between various parameters and functions.

FIG. 6 shows the relationships of the parameters and functions of equation (1). In this figure, x is a particular test position in the waveguide under test, which is determined by the position of the mirror, and is measured from the original point X=0 which is set at the input end of the waveguide under test. In addition, C is a constant, P is the emission power of the light source, T(x) is the transmission coefficient of light from the input end (X=0) to the measurement point X=x, $X=x_k$ is a k-th position of Rayleigh back-scattering point along the waveguide, $a_k$ is the reflection coefficient at that point, $\sigma_0$ is the center wavenumber of the light source, that is, the center frequency divided by the light velocity c, and n is the refractive index of the waveguide. R(X) is a visibility function that represents the visibility of interference fringes of the output light from the light source when the optical path difference is 2 nX. Assuming that E(t) is the electric field of the output light from the light source, and $<>_t$ is a symbol representing the average over a time t, the visibility function R(x) is given by the following equation.

$$R(X) = |<E(t)E^*(t-2nX/c)>_t|/<|E(t)|^2>_t \quad (1)$$

Figure 4:
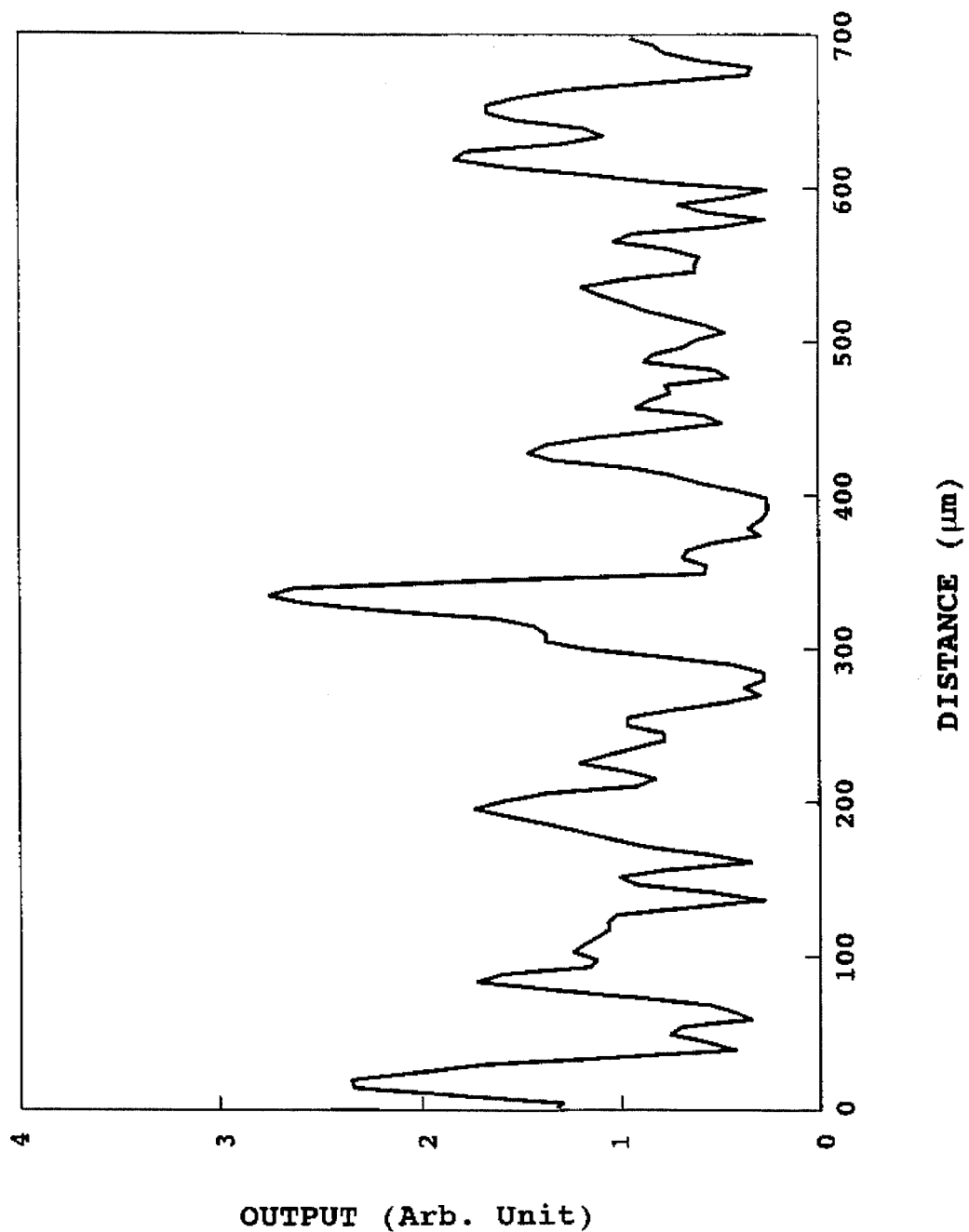
FIG. 4 is a graph illustrating a Rayleigh back-scattered waveform obtained by the optical low coherence reflectometer of FIG. 2.

The purpose of the reflectometer in accordance with the present invention is to obtain the value of a function $T^2(x)$ at each position X=x along the waveguide. For convenience's sake, let us suppose that the function R(X−x) is a rectangular whose width is $\Delta x$ as shown in FIG. 6. Then, a method for obtaining the value of $T^2(x)$ will be as follows: Assuming that the full width at half maximum of the spectrum of the output light from the light source is $\Delta\sigma_0$ in terms of the center wavenumber, the relationship $\Delta x \approx 1/(n\Delta\sigma_0)$ holds. At a particular point X=x, only the scattering particles present in the window $\Gamma(x)$, whose center is X=x and whose width is $\Delta x$, contribute to equation (1). This is because the local oscillator light and the reflected light interfere only in the window width of $\Delta x$ because low-coherent light is used as the light source. Thus, the intensity of a signal detected by the optical low coherence reflectometer is proportional to the total sum of the interference term $a_k a_j \cos[4\pi\sigma_0 n(x_k-x_j)]$ between scattered light generated by scattering particles in the window $\Gamma(x)$. These scattering particles are Rayleigh scattering particles which are distributed randomly along the entire length of the waveguide, and which have submicron correlation lengths. When the width $\Delta x$ of the window $\Gamma(x)$ is of the order of several tens of micrometers, a few micrometer change of x will arise sharp changes in the total sum as shown in FIG. 4.

Here, the average of the Rayleigh back-scattered signals is obtained by sweeping the center wavenumber $\sigma_0$ by $\pm\Delta\sigma/2$ about the center value $\sigma_1$. By integrating I(x) of equation (1) from $\sigma_1-\Delta\sigma/2$ to $\sigma_1+\Delta\sigma/2$ with respect to $\sigma_0$, and by dividing the result by $\Delta\sigma$, the average $<I(x)>$ of I(x) in terms of wavelength is given by the following equation.

$$<I(x)> = CP^2T^2(x) \sum_{k,j} G(n(x_k - x_j))a_k a_j \times \quad (2)$$
$$\cos[4\pi\sigma_1 n(x_k - x_j)]R(x_k - x)R(x_j - x)$$

where T($x_k$) and T($x_j$) are approximated by T(x) because T(x) is supposed to be substantially constant in the width of the window $\Gamma(x)$, that is, in the spatial resolution $\Delta x$. In addition, G(y) is given by the following equation.

$$G(y) = (\sin(2\pi\Delta\sigma y))/(2\pi\Delta\sigma y) \quad (3)$$

As will be seen from equations (1)–(3), the averaging multiplies each interference term in equation (1) by a factor $G(n(x_k-x_j))$, which takes a value 1 at the center $|x_k-x_j|=0$, and sharply reduces to very small values where $|x_k-x_j|>>1/(n\Delta\sigma)$. Therefore, it is only pairs of scattering particles associated with $(x_k-x_j)$, which are present in a range defined by $|x_k-x_j| \leq 1/(n\Delta\sigma) \equiv \Delta L/2$, that actually contribute to $<I(x)>$. Since it is assumed that the change $\Delta\sigma$ due to the sweeping of the center wavelength of the light source is much greater than the spectral width $\Delta\sigma_0$ of the light, $\Delta\sigma >> \Delta\sigma_0$ holds. This means that the width $\Delta L$ associated with $\Delta\sigma$ is much narrower than the width $\Delta x$ of the window $\Gamma(x)$ associated with $\Delta\sigma_0$. In other words, $\Delta L << \Delta x$, as shown in FIG. 6.

Figure 5:
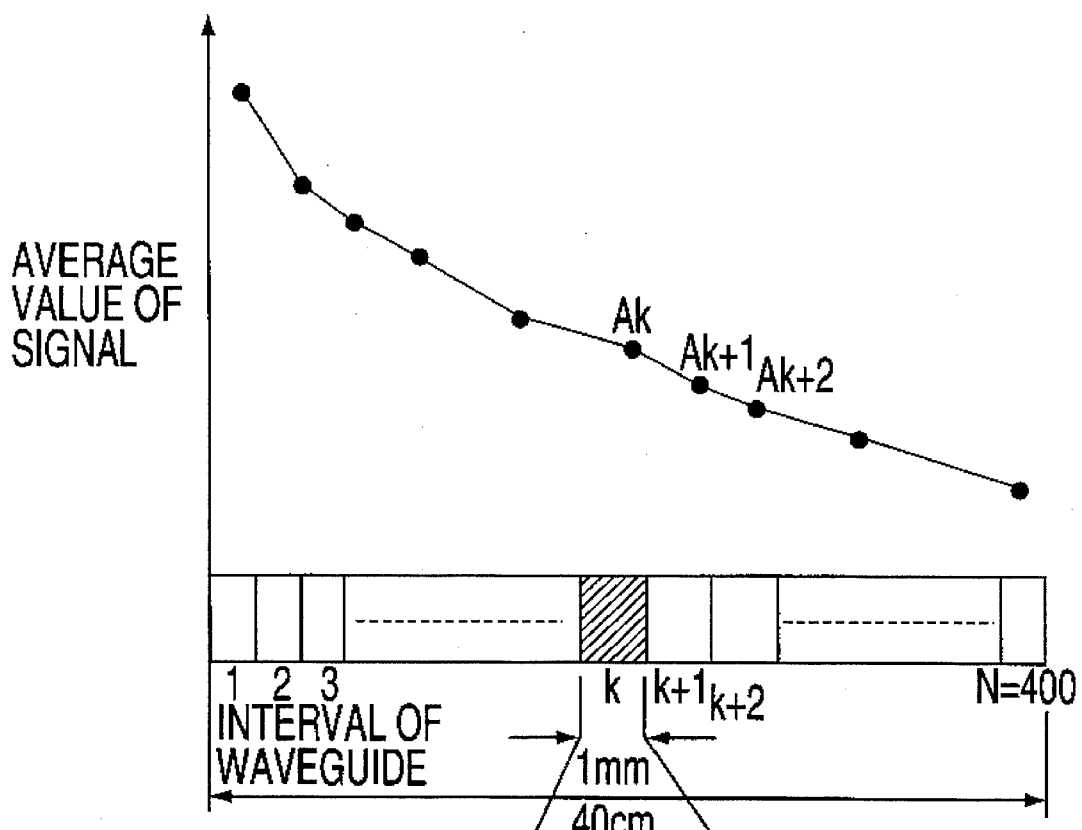
FIGS. 5 and 5A are graphs explaining a conventional smoothing method.
Figure 5A:
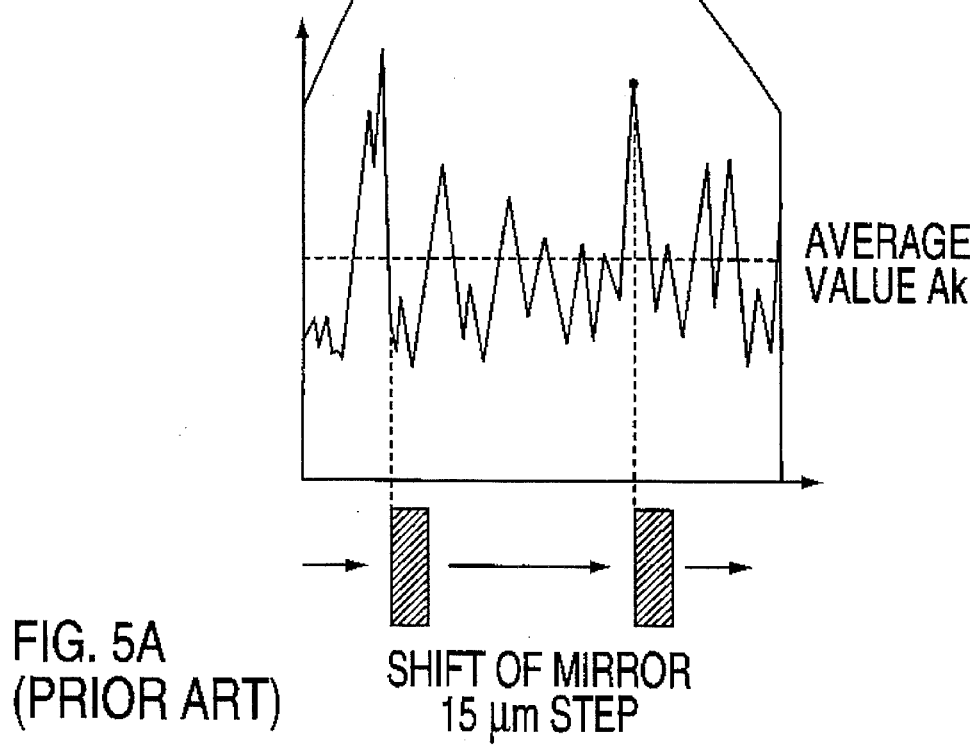

Thus, the right-hand side of equation (2) is equivalent to the following two-step calculations. The first step is to fix $x_k$, and calculate the total sum of the interference terms $a_k a_j \cos[4\pi\sigma_1 n(x_k-x_j)]$ in the window $\Theta(x_k)$ whose center is $x_k$ and whose width is $\Delta L$. The calculation result is assumed to be $\Sigma(\Theta)$. The second step is to calculate the total sum $\Sigma(\Gamma)$ of the $\Sigma(\Theta)$s in the window $\Gamma(x)$ while varying $x_k$. These two steps correspond to the steps of the conventional method as shown in FIG. 5: The first step, in which the total sum $\Sigma(\Theta)$ in the window $\Theta(x_k)$ is calculated, corresponds to detecting the Rayleigh back-scattered signal while fixing the mirror at a position corresponding to $x_k$ in the waveguide under test, when the spatial resolution is $\Delta L$, as described in the conventional technique. The second step, in which the total sum with respect to the window $\Gamma(x)$ is taken, is equivalent to calculate the average value of the Rayleigh back-scattered signals at respective positions in the window $\Gamma(x)$ while shifting the mirror in 15 μm steps in order to shift the detection point in the window $\Gamma(x)$, as described with regard to FIGS. 5 and 5A. Thus, the averaging processing of the Rayleigh back-scattered signals in accordance with the conventional shifting-and-averaging (that is, smoothing) method can be accomplished in an alternative way, in which the center wavelength of the low-coherent light source is swept by an amount $\Delta\sigma$ greater than the spectral width $\Delta\sigma_0$ while fixing the mirror at a position. Since the center wavelength of the low-coherent light source can be easily varied as will be described later, the average Rayleigh back-scattered value can be obtained without carrying out the conventional multi-position measurement accompanying the great number of shifts of the mirror.

If the center wavelength is changed broadly such that the condition of $\Delta\sigma >> \Delta\sigma_0$, that is, $\Delta L << \Delta x$ is satisfied, $G(n(x_k-x_j))$ can be ignored at positions where $x_k-x_j$ is not zero. Accordingly, only the G component associated with $x_k-x_j=0$ contribute to equation (2), and hence, the following equation is obtained.

$$<I(x)> = CP^2T^2(x) \sum_k a_k^2 R^2(x_k - x) \quad (4)$$

By dividing $\Delta x$ by $\Delta L$ (this can be achieved since $\Delta x >> \Delta L$) to obtain N intervals, and assuming that $x_h$ (h=1, 2, ..., N) is the coordinate of the representative point of the h-th interval, equation (4) can be rewritten as follows:

$$<I(x)> = CP^2T^2(x) \sum_h R^2(x_h - x) \sum_k a_k^2 \quad (5)$$

Here, $$\sum_k a_k^2$$

represents the total sum of the scattered intensity $a_k^2$ in the window $\Theta(x_h)$.

As will be described in the following embodiments, $\Delta x$ is on the order of a few millimeters, and $\Delta L$ is on the order of several tens of microns. With regard to Rayleigh scattering particles, although $a_k$ changes randomly at a correlation length of submicron, the square sum $$\sum_k a_k^2$$

in ΔL of several tens of microns takes a constant value over the waveguide. By changing the summation with respect to h to the integral with respect to Xh, the factor $$\sum_h R^2(x_n - x)$$

is proved to be proportional to $$\int_{-\infty}^{\infty} R^2(x_h - x) dx_h$$

which is determined uniquely by the spectrum of the output light from the low-coherent light source. Since the spectrum of the light at each wavelength is kept identical during the wavelength sweep, this factor is also kept constant during the sweep. Therefore, <I(x)> of equation (5) is proportional to $T^2(x)$. Thus, $T^2(x)$ can be obtained by measuring <I(x)> while varying x.

In practice, since the sweeping width of the center wavelength is generally limited by the gain width of the optical amplifier employed in the light source, some randomly changing components will remain with the change of x. This residual components, however, will fall below ±1 dB of the average value given by equation (5).

The averaging can be carried out by calculating $$<I(x)> = \sum_k I_k/N$$

at individual positions x, where N is the number of wavelengths occurring during a sweep, and $I_k$ is the signal associated with a wavelength $\lambda_k$. In addition, since I(x) is proportional to $P^2$, if the power P of the light source varies for each wavelength, $$\sum_k I_k(P_i/P_k)^2/N$$

should be calculated, where $P_i$ and $P_k$ are optical outputs at wavelengths $\lambda_i$ and $\lambda_k$, and $\lambda_i$ is a particular wavelength in a number of wavelengths $\lambda_1, \lambda_2, \ldots, \lambda_N$.

To accomplish the purpose, the present invention is characterized in the following:

(1) The speckle noise is reduced by using a low-coherent light source whose center wavelength is tunable, and by averaging Rayleigh back-scattered signals for individual wavelengths.

(2) The wavelength tunable, low-coherent light source is implemented by using one or two optical amplifiers one or two optical bandpass filters. The superfluorescent light emitted from the optical amplifier is bandpassed by the first optical bandpass filter, optically amplified, and bandpassed again by the second bandpass filter in order to remove the spontaneous emission light contained in the amplified light. The center wavelengths of transmission of both the bandpass filters are changed so that they agree with each other.

Next, embodiments in accordance with the present invention will be described referring to the drawings.

EMBODIMENT 1

Figure 7:
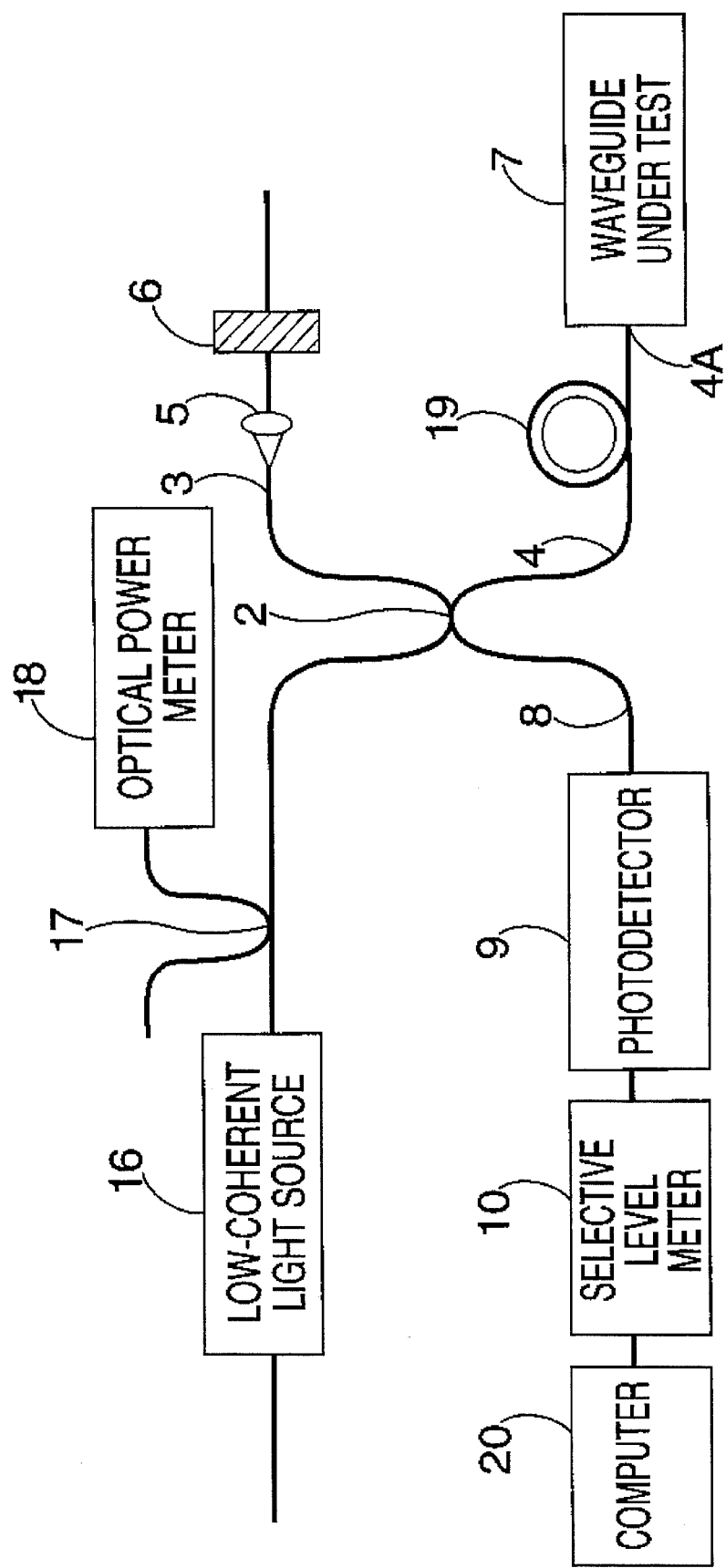
FIG. 7 is a block diagram showing a reflectometer of a first embodiment in accordance with the present invention.

FIG. 7 shows a reflectometer of a first embodiment in accordance with the present invention. In this figure, the reference numeral 16 designates a low-coherent light source whose center wavelength is tunable, 17 designates an optical fiber coupler for monitoring the output light from the light source 16, 18 designates an optical power meter, 19 designates a phase modulator, and 20 designates a computer. The phase modulator 19 is constructed by winding a part of the probe fiber 4 around a cylindrical PZT (lead zirconate titanate) piezoelectric stretcher. It generates a carrier of 140 Hz as a serrodyne does, by applying a sawtooth waveform voltage of 140 Hz. In this embodiment, the intensity I(x) of Rayleigh back-scattered light from the waveguide 7 under test is measured by detecting the 140 Hz component in the output from the optical detector 9 with the selective level meter 10 at each position x of the mirror 6.

The present invention carries out the following two types of wavelength averaging processings for wavelength changes of the light source 16.

(1) The first averaging method calculates $$<I(x)> = \sum_k I_k(P_i/P_k)^2/N$$

at each position x after sweeping the entire wavelength range once, during which the monitor output $P_k$ from the optical power meter 18 and the output $I_k$ from the selective level meter 10 are stored in the computer 20 for each wavelength $\lambda_k$ while sequentially changing the wavelength of the light source 16. Here, $P_i$ is optical output power at a particular wavelength $\lambda i$ among the wavelengths $\lambda_k$ (k=1, 2, ..., N) occurring during the sweep of the wavelength.

(2) The second averaging method sweeps the wavelength of the light source at a fixed interval, and controls the output power of the light source so that it is maintained at a constant value.

The first method requires no feedback control mechanism for maintaining the output power of the light source at a constant value. Accordingly, the first method has the advantage over the second method in that the effect of output fluctuations can be easily corrected. The first method, however, takes a considerable time because $I_k$ and $P_k$ for each wavelength must be stored in the computer 20, and averaged for each sweep.

Figure 8:
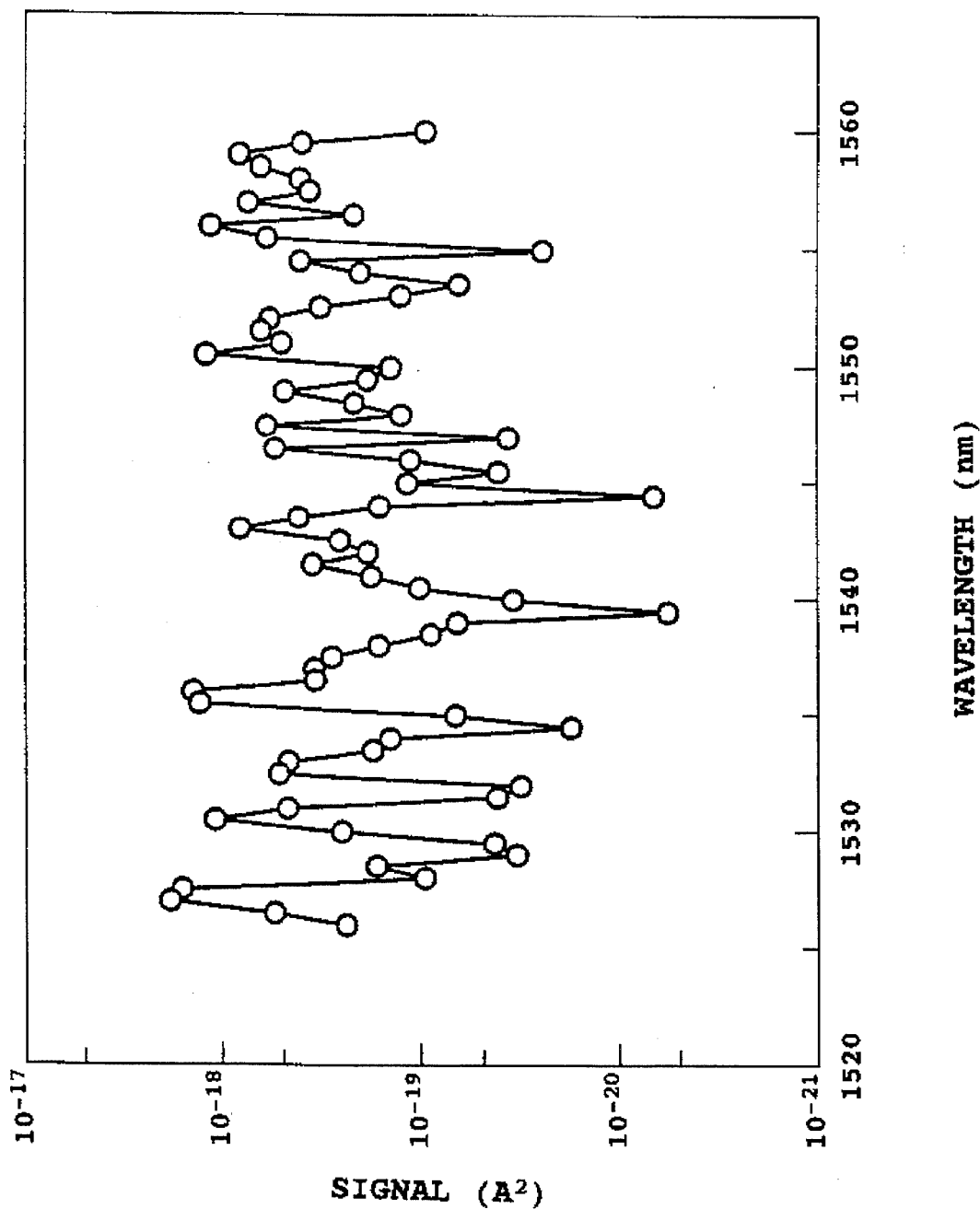
FIG. 8 is a graph illustrating changes in a Rayleigh back-scattered signal when the wavelength of a light source is varied.

FIG. 8 illustrates changes in Rayleigh back-scattered signals when the wavelength of the probe light is varied from 1525 nm to 1560 nm at 1 nm interval. Although the signals change randomly at this interval of the wavelength, the average value of the Rayleigh back-scattered signals at each position along the waveguide can be obtained by averaging the signal.

Figure 9:
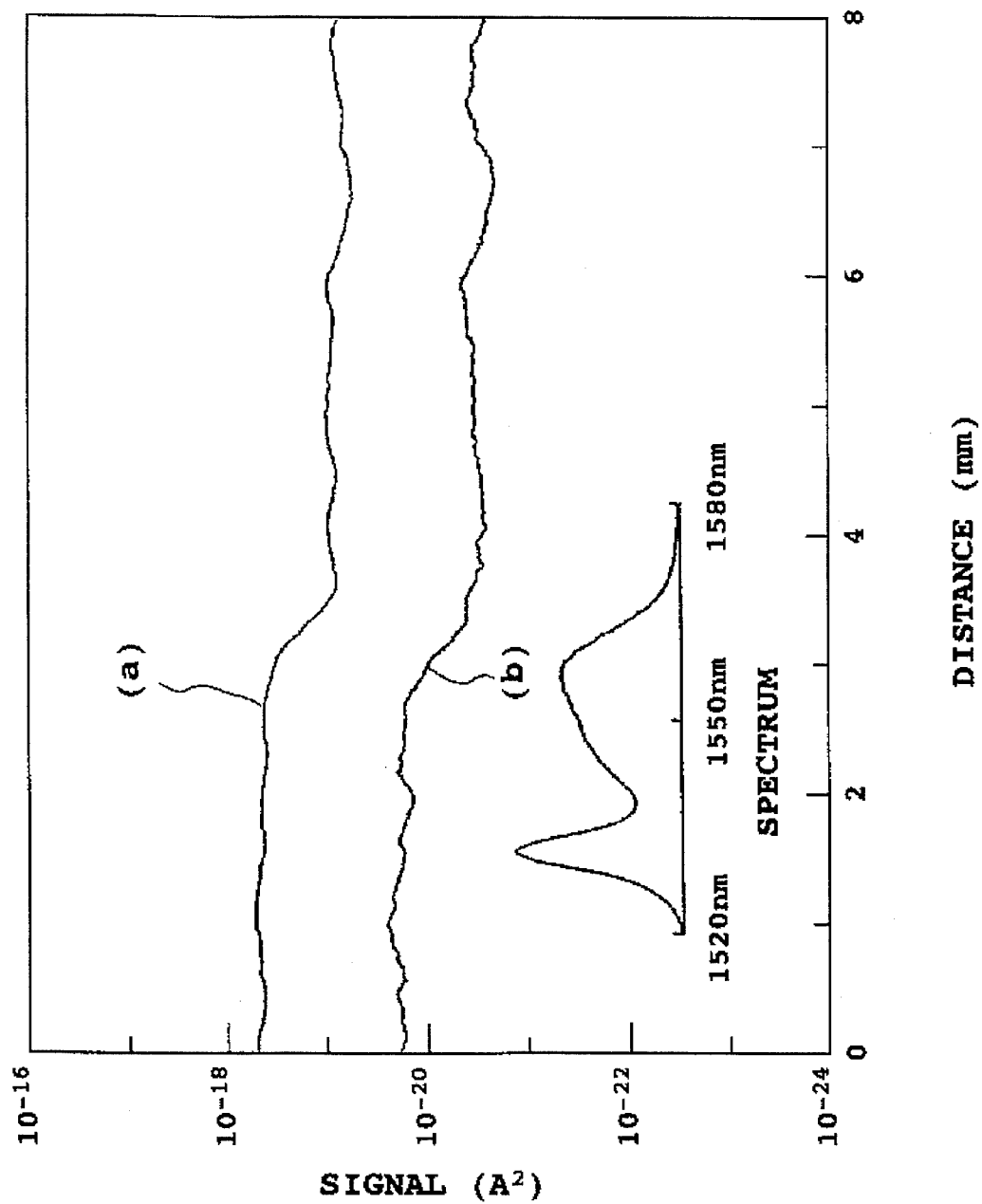
FIG. 9 is a graph showing Rayleigh back-scattering intensity obtained by (a) a wavelength averaging method in accordance with the present invention, and (b) the conventional smoothing method.

In FIG. 9, (a) illustrates an averaged Rayleigh back-scattered profile from a spliced single mode fiber. An optical power loss of the order of a few dBs occurred at the position of 3 mm, at which two optical fibers were spliced. The fluctuations of the Rayleigh back-scattered signal were within ±1 dB. Thus, the splice loss was estimated on the basis of the changes of the signal at the spliced point. In this figure, (b) illustrates a Rayleigh back-scattered profile obtained by the conventional smoothing method. In this measurement, the superfluorescent light from an optical fiber amplifier, whose spectrum is shown in the inset of FIG. 9, was used as the light source, and the Rayleigh back-scattered signals detected were smoothed along the length of the waveguide. The optical output power from the light sources in both the measurements was 4.3 dBm.

Comparing (a) and (b) of FIG. 9, it will be seen that the waveform obtained by the wavelength averaging method in accordance with the present invention fluctuates less than that obtained by the conventional smoothing method. Furthermore, the signal level of the present invention is higher than that of the conventional method by an amount of 14 dB. Thus, the wavelength averaging method in accordance with the present invention is superior to the conventional method not only in reducing fluctuations but also in increasing the signal.

Figure 10:
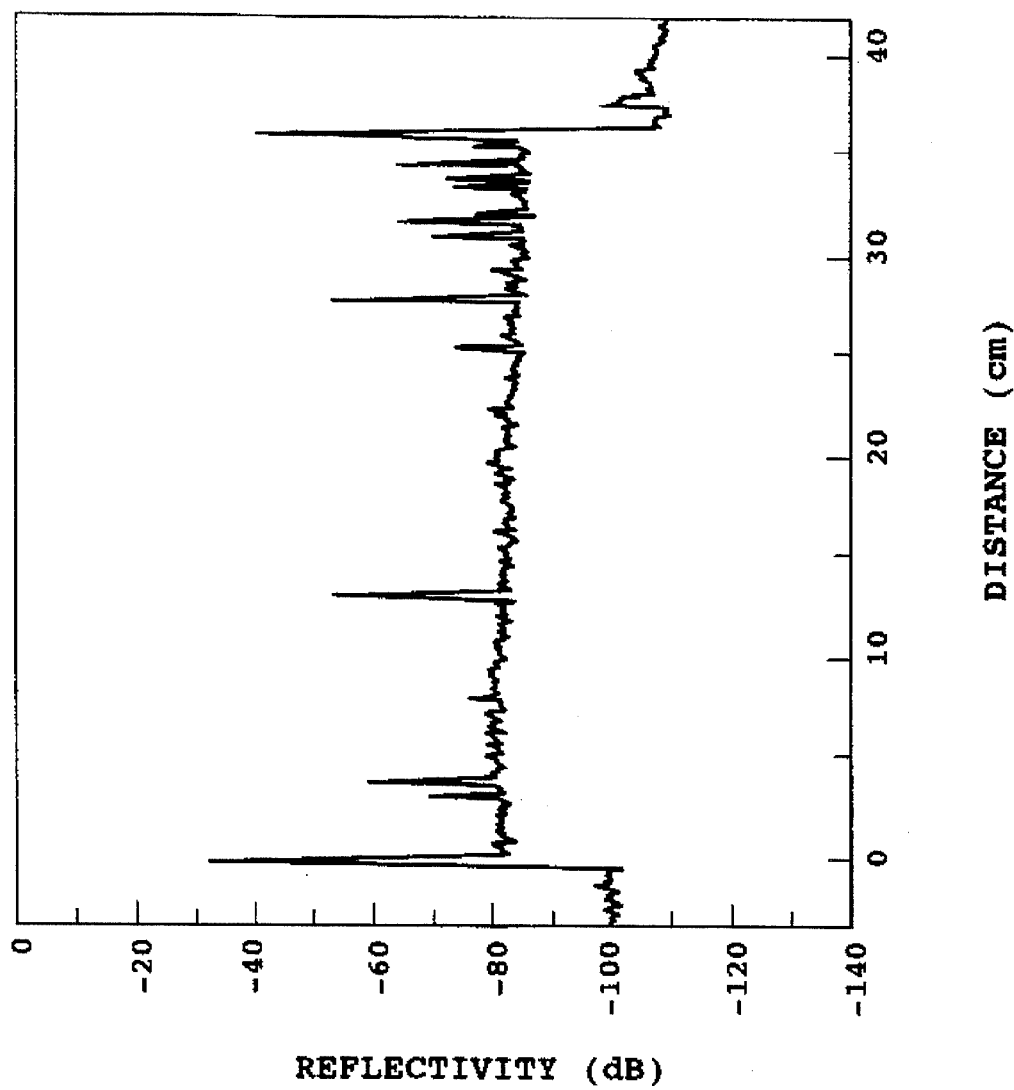
FIGS. 10 and 11 are graphs illustrating Rayleigh back-scattering intensity of silica-based planar lightwave circuits.
Figure 11:
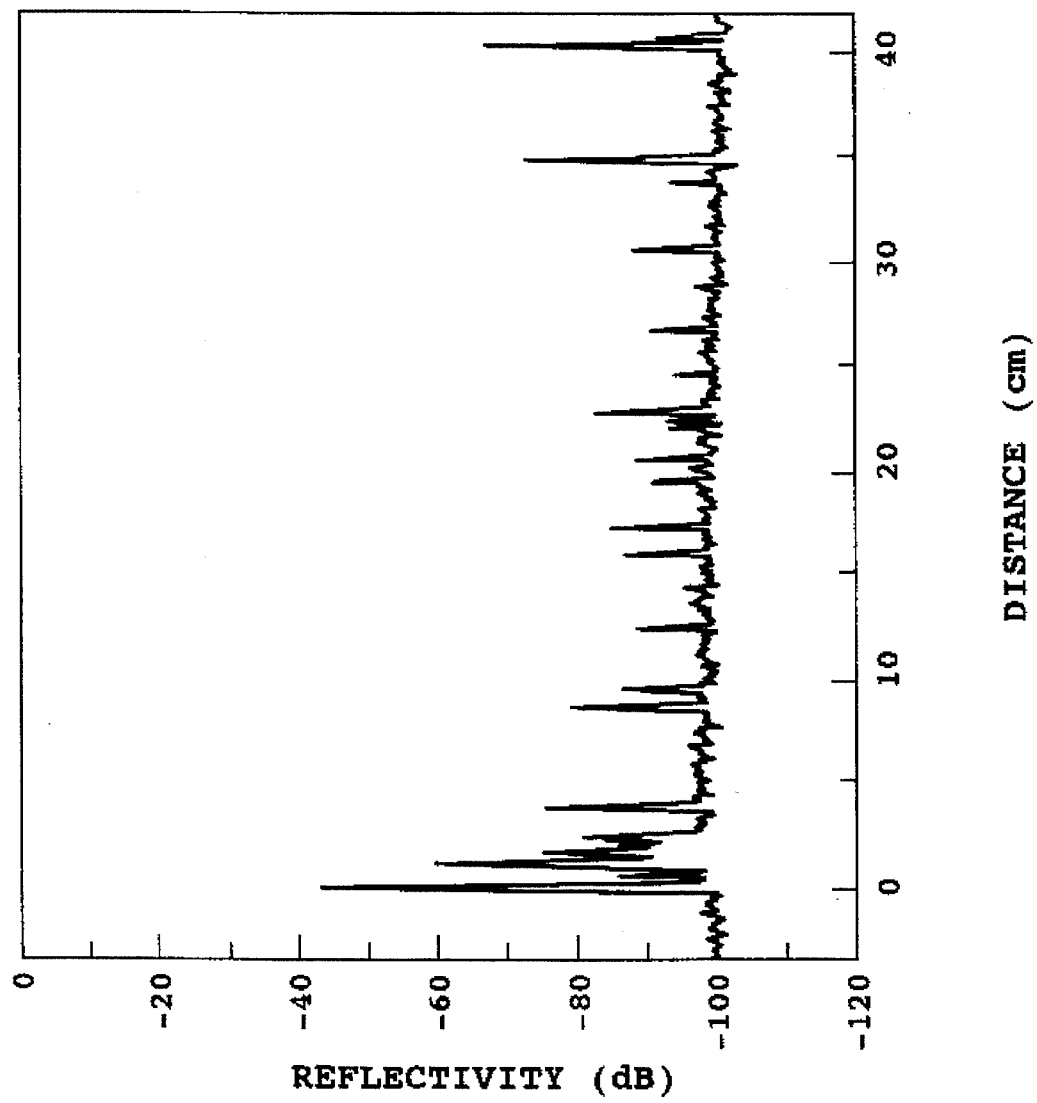

FIGS. 10 and 11 illustrate results of measurement of the Rayleigh back-scattered profile of silica-based planar lightwave circuits. In the measurement, the TE mode was excited at the input end of each waveguide (lightwave circuit). Each waveguide was connected to optical fibers on the input and output facets of the waveguide via index matching oil applied to their end faces. The index matching oil, however, could not perfectly eliminate end-reflection, and a residual reflection of approximately −30 dB was observed. On the other hand, the reflectivity of the Rayleigh back-scattering was less than −80 dB. In spite of such a large Fresnel reflection, it was observed that the Rayleigh back-scattering was attenuated by an amount of 5 dB in 35 cm. Thus, it was found that the loss coefficient of the waveguide was (5 dB /35 cm)/2= 0.07 dB/cm.

In FIG. 11, the Rayleigh back-scattered signal was attenuated by an amount of 0.7 dB over 23 cm in the first half of the waveguide, and by an amount of 2.2 dB over 17 cm in the latter half of the waveguide. Thus, the loss coefficients of each portion was estimated as (0.7 dB/23 cm)/2=0.015 dB/cm, and (2.2 dB/17 cm)/2=0.06 dB/cm.

The second averaging method is implemented by providing the light source with a control system for maintaining the output power of the light source at a constant value while sweeping the wavelength of the light source at a fixed period. More specifically, the output of the light source 16 is split by the coupler 17 of FIG. 7 so that the temporal variation in the output power of the light source 16 is detected, and the pumping power of the light source 16 is controlled so that the output power is kept constant. In this case, signal changes as shown in FIG. 8 are observed for each one period of the sweep of the wavelength. Assuming that the period of the sweep is 100 ms, the signal changes at least at a rate ten times that of the period, that is, at approximately 10 ms. Accordingly, if the cutoff frequency of the lowpass filter, which is incorporated in the selective level meter 10, is set at 3 Hz (that is, if the response speed is set at about 0.3 s), the signal whose changing rate is higher is smoothed by the lowpass filter, and the average value of the signal is outputted as a DC component.

Here, it should be noticed that the detection frequency of the reflectometer should be changed from 140 Hz to several tens of kHz. This change can be performed by incorporating another PZT stretcher driven by a 10 kHz sinusoidal waveform voltage into a local oscillator port 3 in FIG. 7, or by replacing the PZT stretcher 19 with a waveguide phase shifter such as an LiNbO$_3$ waveguide shifter driven by a 10 kHz sawtooth waveform voltage.

In this second method, although the feedback mechanism connected to the light source will complicate the system, the time required for obtaining an average Rayleigh back-scattered signal at each one point along the waveguide can be reduced to approximately 1 sec, by setting the wavelength sweep period at approximately 100 ms. In contrast, the conventional method, which smoothes the Rayleigh back-scattered signals along the length of the waveguide after performing multi-point measurements while shifting the mirror, takes approximately 100 seconds to obtain one average Rayleigh back-scattered signal, under the assumption that the measurement at one point takes 1 second and the total of 100 neighboring point measurements are necessary to obtain one average value.

EMBODIMENT 2

Figure 12:
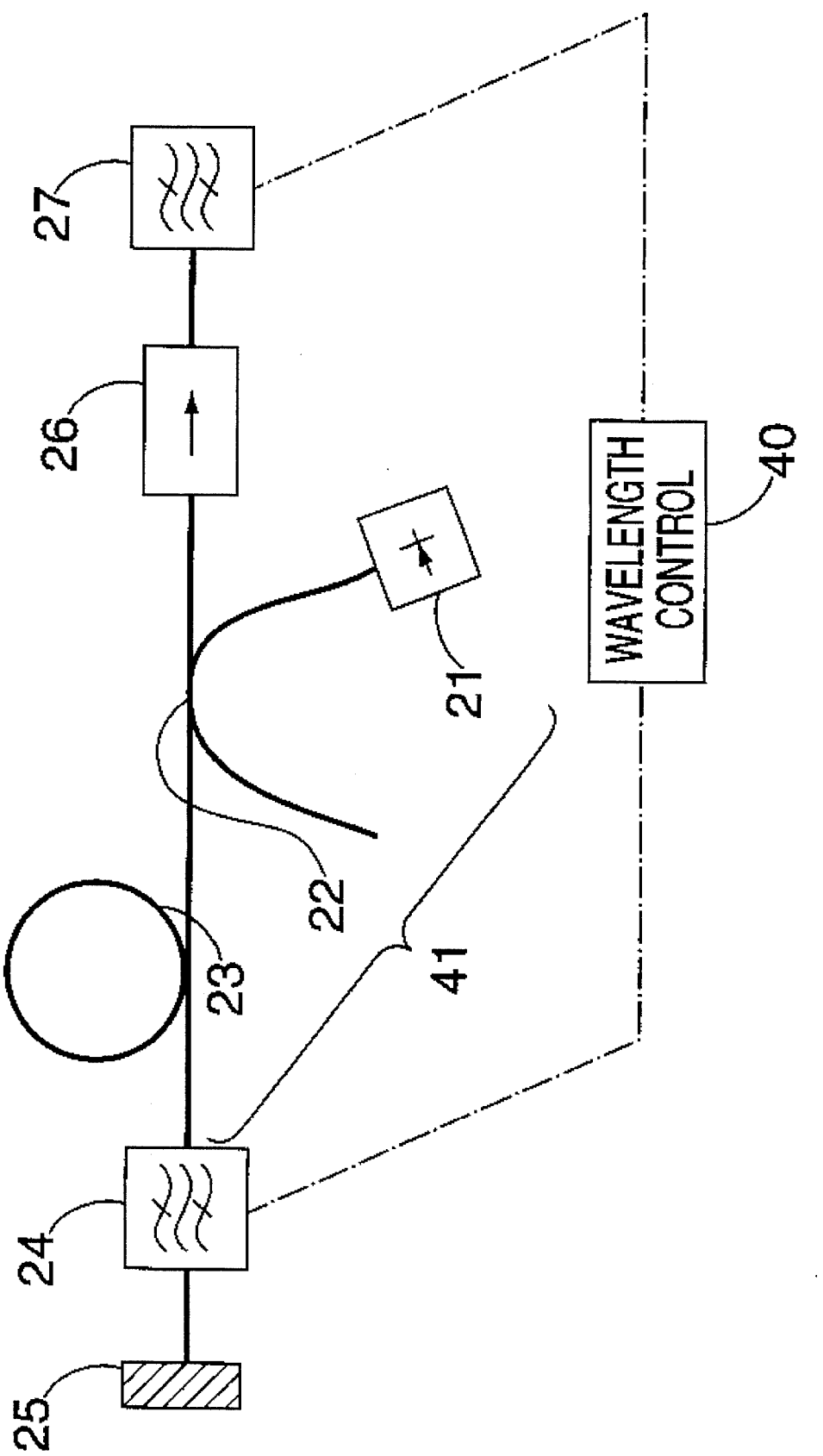
FIG. 12 is a block diagram showing a light source of a second embodiment in accordance with the present invention.

FIG. 12 shows a second embodiment in accordance with the present invention, which implements a tunable wavelength superfluorescent light source for a reflectometer. In this figure, the reference numeral 21 designates a pump source whose wavelength is 1.48 μm, 22 designates a wavelength-division multiplexer coupler for wavelengths of 1.55 μm and 1.48 μm, 23 designates an erbium-doped optical fiber, 24 designates an optical bandpass filter module with optical fibers attached to its ends, 25 designates a mirror, 26 designates an optical isolator, 27 designates an optical bandpass filter module identical to the filter module 24. The superfluorescent light emitted from an optical amplifier 41, which is composed of the erbium-doped optical fiber 23, the pump source 21, and the WDM coupler 22, is passed through the optical bandpass filter module 24, and is reflected on the mirror 25. The reflected light passes through the optical bandpass filter 24, again, and enters the optical fiber amplifier 41 to be amplified.

The optical bandpass filter 24 includes a bulk-type filter, a collimate lens, and optical fibers. The bulk-type filter has bandpass characteristics whose width is 0.5 nm at the center wavelength of 1560 nm for vertically incident light, and approximately 1 nm about the wavelength of 1530 nm. The optical bandpass filter 24 shifts the center wavelength of the passband toward the short wavelength side when the filter 24 is rotated to change the incident angle of the light beam. The optical isolator 26 is provided to suppress the laser oscillation. Since the low-coherent light amplified by the optical amplifier 41 and emitted from the optical isolator 26 contains spontaneous emission light caused by the amplification, it must be removed by the optical bandpass filter module 27. By rotating the two bandpass filters 24 and 27 in synchronism, low-coherent light whose width is less than 1 nm is obtained over a range of more than 30 nm width. The rotation of the bandpass filters 24 and 27 are carried out by a wavelength control mechanism 40.

Although the light source as shown in FIG. 12 can easily vary the wavelength, it has the following two drawbacks.

(1) In the setup of FIG. 12, the light output is limited to a few milliwatts at most, because an increase in the pumping power of the pump source 21 to increase the optical output will cause the laser oscillation. The setup can be considered as a Fabry-Perot resonator, in which the optical fiber amplifier 41 is sandwiched between the mirror 25 and the optical isolator 26. Since the reflectivity of the mirror 25 is nearly 100%, the return loss caused by a round trip of light between the mirror 25 and the amplifier 41 is approximately 3 dB at most, even if the loss of the bandpass filter 24 is taken into account. On the other hand, the return loss of the optical isolator 26 is no more than 60 dB in the state of the art. Accordingly, the loss which the light undergoes during the round trip in the Fabry-Perot resonator is approximately 3 dB+60 dB=63 dB. In contrast with this, since the one-way gain of the optical fiber amplifier reaches 40 dB when the pumping power is increased, the two-way gain thereof approaches 80 dB. As a result, an increase in the pumping power will cause the laser oscillation because the gain exceeds the loss in this setup.

(2) Even if the laser oscillation is suppressed by limiting the pumping power, gain near the loss will cause fine structure in the spectrum of the emitted light because the optical feedback effect cannot be ignored. This will cause complicated side lobes in a measurement of Fresnel reflection using a optical low coherence reflectometer. More specifically, Fresnel reflection occurs at the interface when light enters a medium having a different index of refraction. Accordingly, it can be assumed that the reflection coefficient at the interface $x_k$ is $a_k$, whereas the reflection coefficients at positions other than $x_k$ can be neglected. Thus, by substituting $a_k$ in equation (2) for $a\delta(X-x_k)$, where a is a constant, and $\delta$ is the delta function, and replacing $\Sigma$ by integral, measurement of Fresnel reflection by a optical low coherence reflectometer corresponds to measuring $R^2(x)$, the square of the visibility function $R(x)$ of the output light from the light source. This square function is referred to as a Fresnel response function. Since $R(x)$ is determined by the Fourier transform of the spectrum of the light source, the fine structure in the spectrum will cause complicated side lobes in the Fresnel response function.

The level of the Rayleigh back-scattered signal, which is reflected by the waveguide 7 under test and is detected by the detector 9, is less than −80 dB as illustrated in FIGS. 10 and 11, when the back-scattered signal is measured at about 1 mm resolution. More than 10 mW optical output is essential to the light source in order to measure such a weak signal at a high S/N (signal-to-noise ratio). Generally speaking, since the refractive index of the waveguide differs from that of the probe optical fiber 4 in FIG. 7, it is impossible to reduce the end-reflection (Fresnel reflection) of the waveguide to an order of the level of the Rayleigh back-scattered signal by using index matching oil. Since the length of the waveguide 7 under test is no more than 1 m, the Fresnel response signal to the residual Fresnel reflection will be accompanied with side lobes as described in (2) above. Thus, the Rayleigh back-scattered signals from a larger part of the waveguide 7 under test will be masked by the side lobes, and hence, measurement of the Rayleigh back-scattered signals becomes impossible. The next embodiment of the light source as shown in FIG. 13 is proposed to overcome this problem.

EMBODIMENT 3

Figure 13:
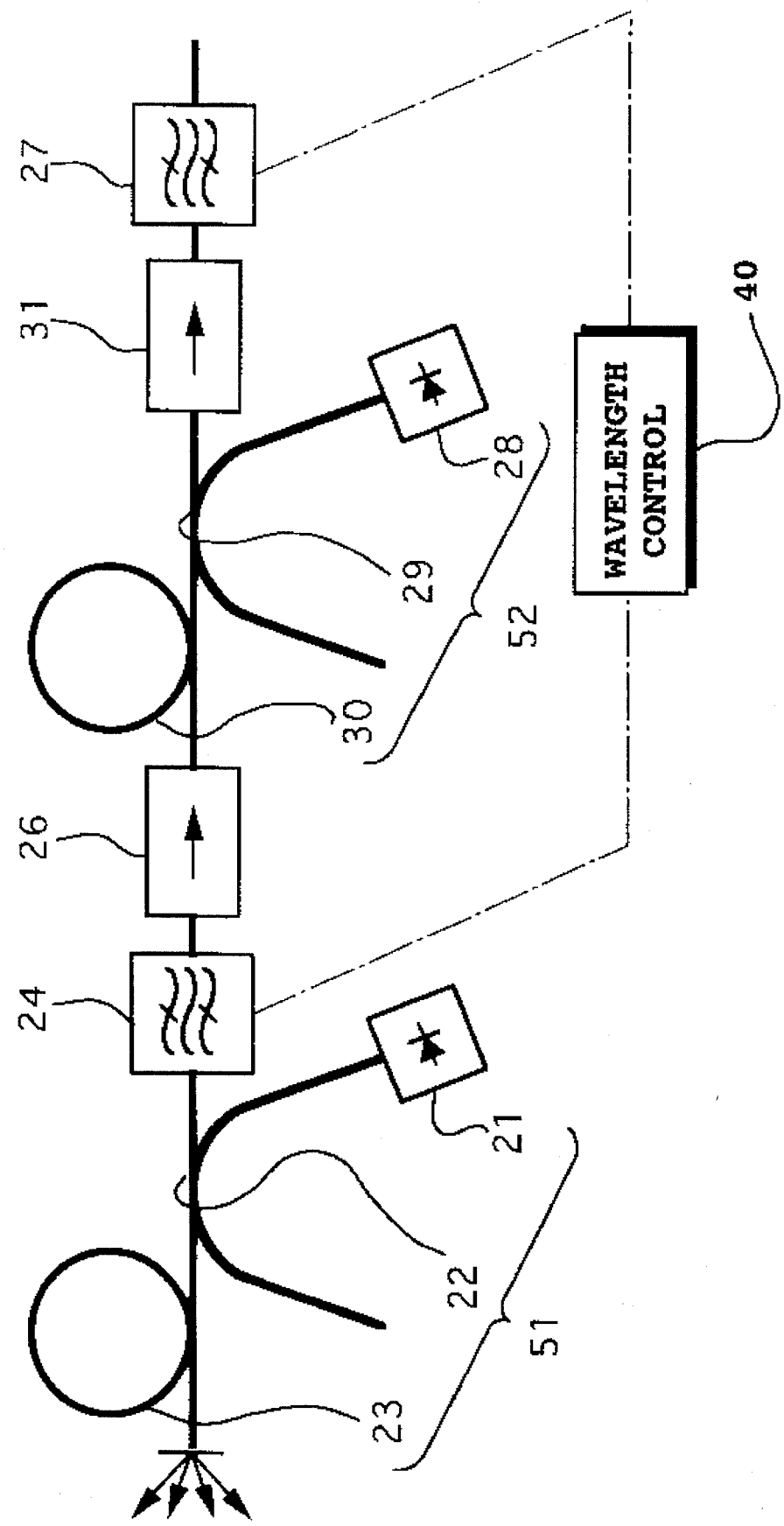
FIG. 13 is a block diagram showing a light source of a third embodiment in accordance with the present invention.

FIG. 13 shows a third embodiment proposed to solve the problem of the preceding embodiment 2. This problem arises from the fact that the portion for generating the low-coherent light, whose bandwidth is narrower than that of the superfluorescent light emitted from the optical amplifier, and the portion for amplifying light are common as shown in FIG. 12.

In view of this, this embodiment uses two optical amplifiers 51 and 52, which are optically interconnected in such a manner that the laser oscillation is suppressed by optical isolators. The first optical amplifier 51 is used to generate low-coherent light whose spectral width is narrower than that of the superfluorescent light from the amplifier. The second optical amplifier 52 amplifies the light, which is emitted from the first amplifier 51, and is passed through an optical bandpass filter 24 and an optical isolator 26. The optical isolator 26 serves to isolate the two optical amplifiers 51 and 52, thereby suppressing the optical feedback effect greatly.

In FIG. 13, the reference numeral 21 designates a pump source module whose wavelength is 1.48 μm, 22 designates a WDM (Wavelength-Division Multiplexer) coupler for 1.48 μm and 1.55 μm, 23 designates an erbium-doped optical fiber, 24 and 27 each designate an optical bandpass filter module, 28 designates a pump source module whose wavelength is 1.48 μm, 29 designates a WDM coupler, 30 designates an erbium-doped optical fiber, and 31 designates an optical isolator.

The optical bandpass filter module 24 is provided for generating low-coherent light from the superfluorescent light produced by the first optical fiber amplifier 51, which is composed of the elements 21, 22 and 23. The low-coherent light has a bandwidth narrower than the spectral width of the superfluorescent light. One end of the optical fiber 23 is cut, thereby giving return loss of 60 dB. The total return loss of the optical isolator 26 and the optical bandpass filter 24 is also 60 dB. Therefore, the light undergoes the total of approximately 120 dB loss during a round trip in the Fabry-Perot resonator which is set up between the optical isolator 26 and the cut end of the optical fiber 23. The loss greatly exceeds the gain of the optical amplifier 51, which is 80 dB. Therefore, the effect of the optical feedback can be greatly reduced.

The narrow-band, low-coherent light is amplified by the second optical amplifier 52 which is composed of the elements 28, 29 and 30, and is sandwiched between the optical isolators 26 and 31. Since the second optical amplifier 52 is sandwiched between the optical isolators 26 and 31, whose return loss is 60 dB, respectively, the effect of the optical feedback can be greatly reduced as in the first optical amplifier 51. The narrow-band light, which is amplified by the second optical amplifier 52, is passed through the second optical bandpass filter 27, so that wideband superfluorescent light generated by the second optical amplifier 52 is removed. In an experiment, the optical bandpass filter modules 24 and 27 are tuned by the wavelength control mechanism 40 so that their center wavelengths of the passband agree with each other.

Figure 14:
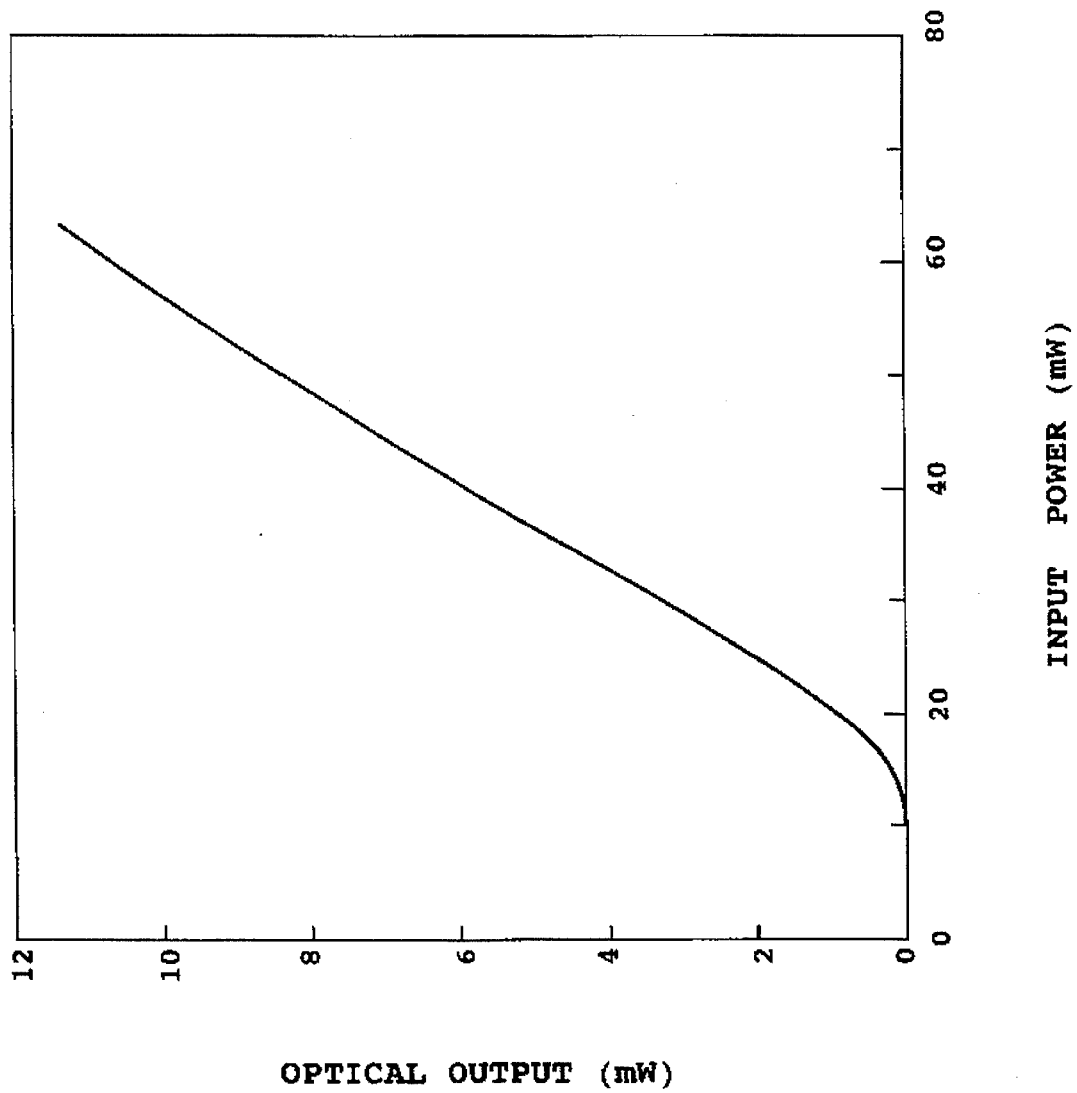
FIG. 14 is a graph illustrating pump input versus optical output power of the light source of FIG. 13.

FIG. 14 illustrates the optical output power from the optical bandpass filter 27 against the pumping input power to the second optical amplifier 52. Here, the wavelength of the input was 1.48 μm (1480 nm), and the center wavelength of the output was 1555 nm. Since the optical isolators 26 and 31 are a polarization-independent type in this embodiment, the output light was in nearly an unpolarized state. The optical output power of approximately 11 mW was obtained for 60 mW pumping power as shown in FIG. 14.

Figure 15:
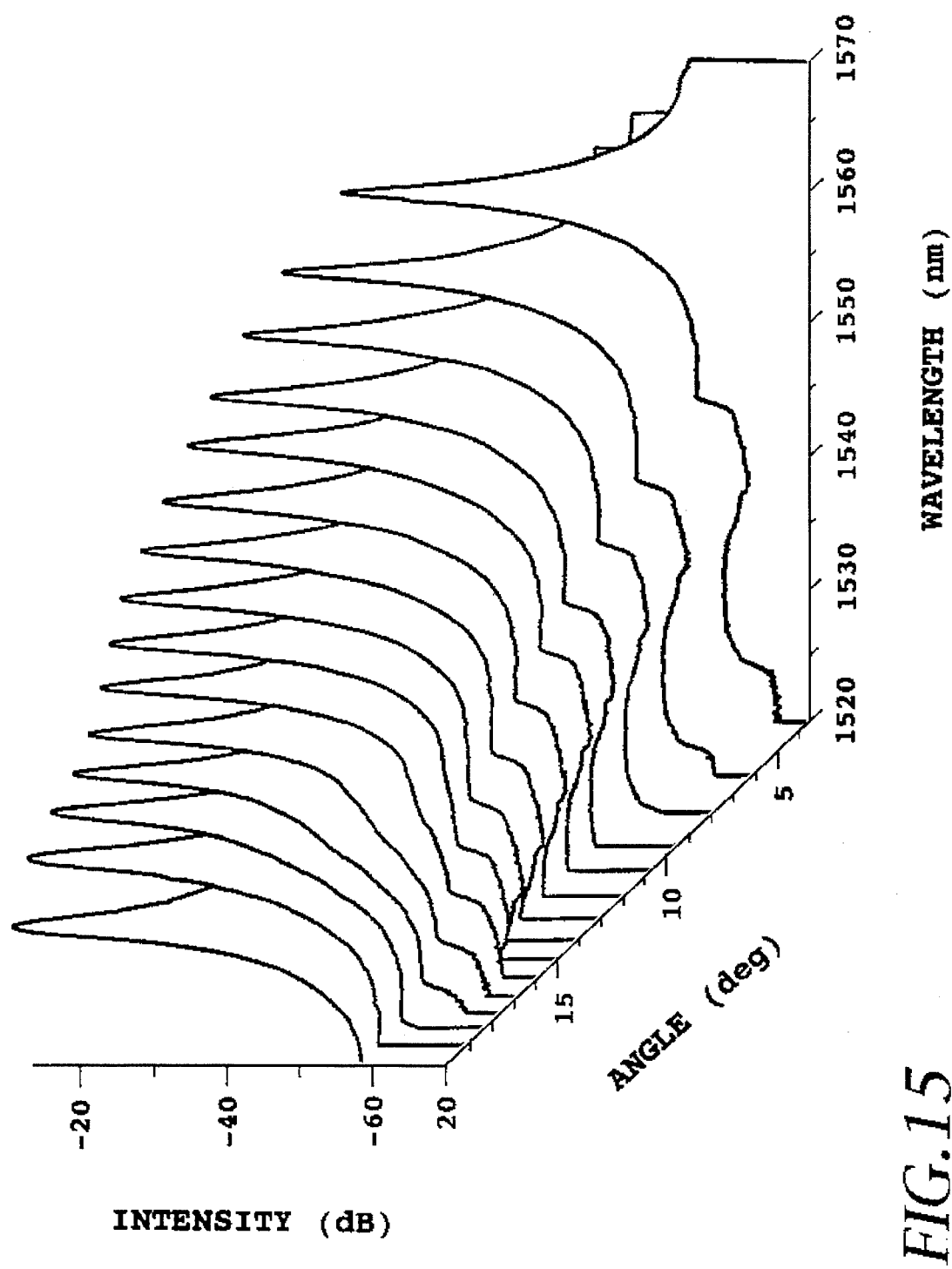
FIG. 15 is a graph illustrating changes in the output spectrum when the rotation angle of the optical filters is varied in the light source as shown in FIG. 13.

FIG. 15 illustrates the optical spectra of the output light in a logarithmic scale, when the pumping input power to the optical amplifier 52 is set at 60 mW, and the center wavelengths of the passband of the optical bandpass filters 24 and 27 are varied from 1530 nm to 1560 nm in 2 nm steps by rotating dielectric coating filters incorporated into the optical bandpass filters 24 and 27. The rotation angle in FIG. 15 is the rotation angle of the dielectric coating filter of the optical bandpass filter 27. The pumping input power to the first optical fiber amplifier 51 was 60 mW in FIGS. 14 and 15. As shown in FIG. 15, the output light is a narrow-band, low-coherent light whose bandwidth is equal to or less than 1 nm at any wavelengths. Thus, the light source of this embodiment can produce high-power, narrow-bandwidth, low-coherent light without causing the laser oscillation, even if the pumping input power to the optical amplifiers 51 and 52 is 60 mW, and the one-way gain of the optical amplifiers is increased to near 40 dB.

Figure 16:
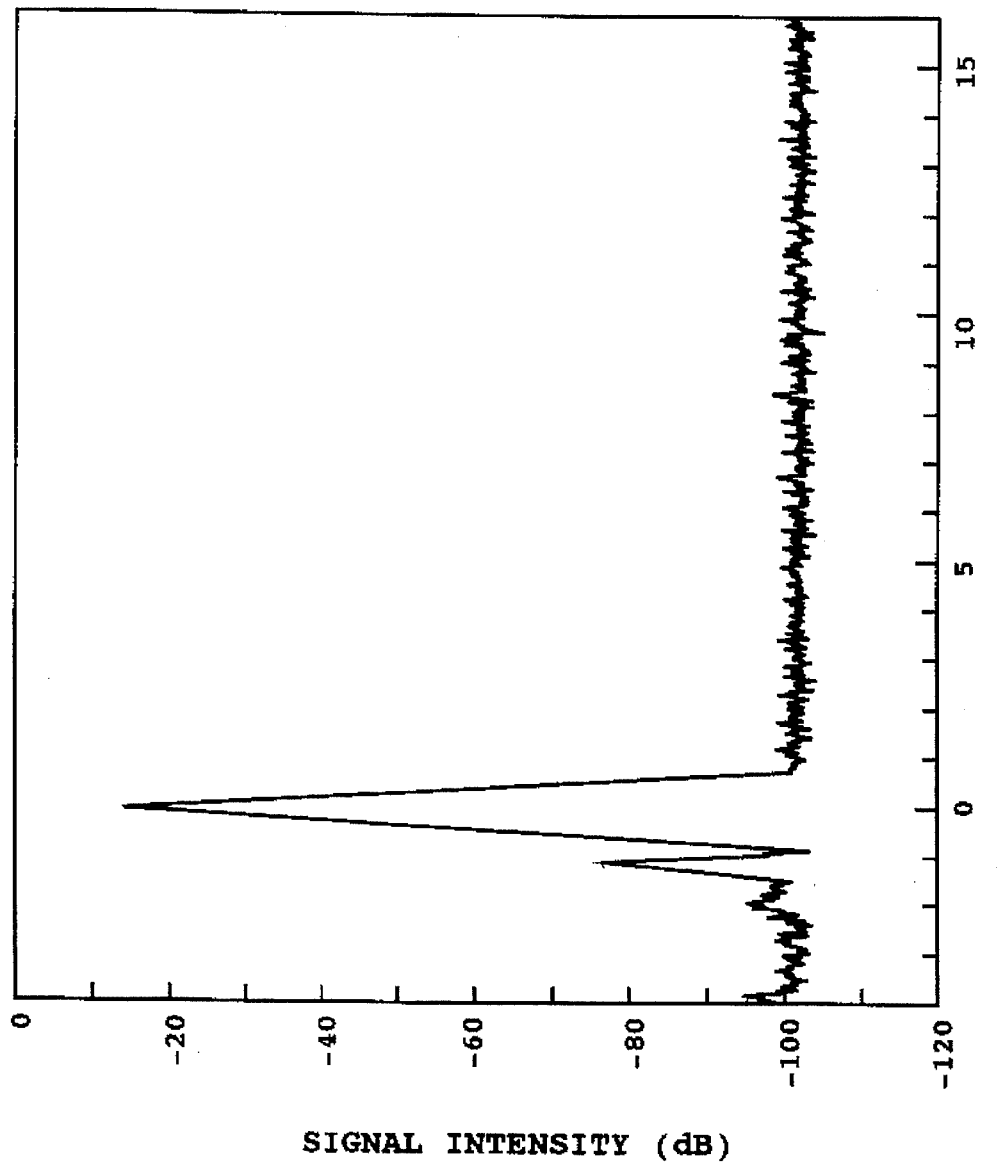
FIG. 16 is a graph illustrating a response function of a reflectometer with respect to the path length change of local oscillator light.

FIG. 16 shows a measurement result of the Fresnel response function of the optical low coherence reflectometer by using a −15 dB Fresnel reflection occurring at the output end 4A (see, FIG. 7) of the probe optical fiber 4 with the waveguide 7 under test removed. In FIG. 16, the output from the reflectometer is represented in dB, with the output scale being adjusted so that the output becomes −15 dB when the optical path length difference is zero. As described above, measuring the Fresnel reflection with the optical low coherence reflectometer corresponds to measuring the square $R^2(x)$ of the visibility function $R(x)$ of the output light from the light source. The square function is called a Fresnel response function. Accordingly, the waveform of FIG. 16 represents values of the function $10\log_{10}R^2(x)-15$. The Fresnel response function comes to have complicated side lobes if the optical feedback is present in the light source, because the feedback will cause fine structure in the output spectrum from the light source. In this measurement, the center wavelength of the output light from the light source was 1555 nm, and the output power was 11 mW. In FIG. 16, the axis of abscissas represents changes in the optical path length of the local oscillator light due to the movement of the mirror 6 of FIG. 7.

Figure 1:
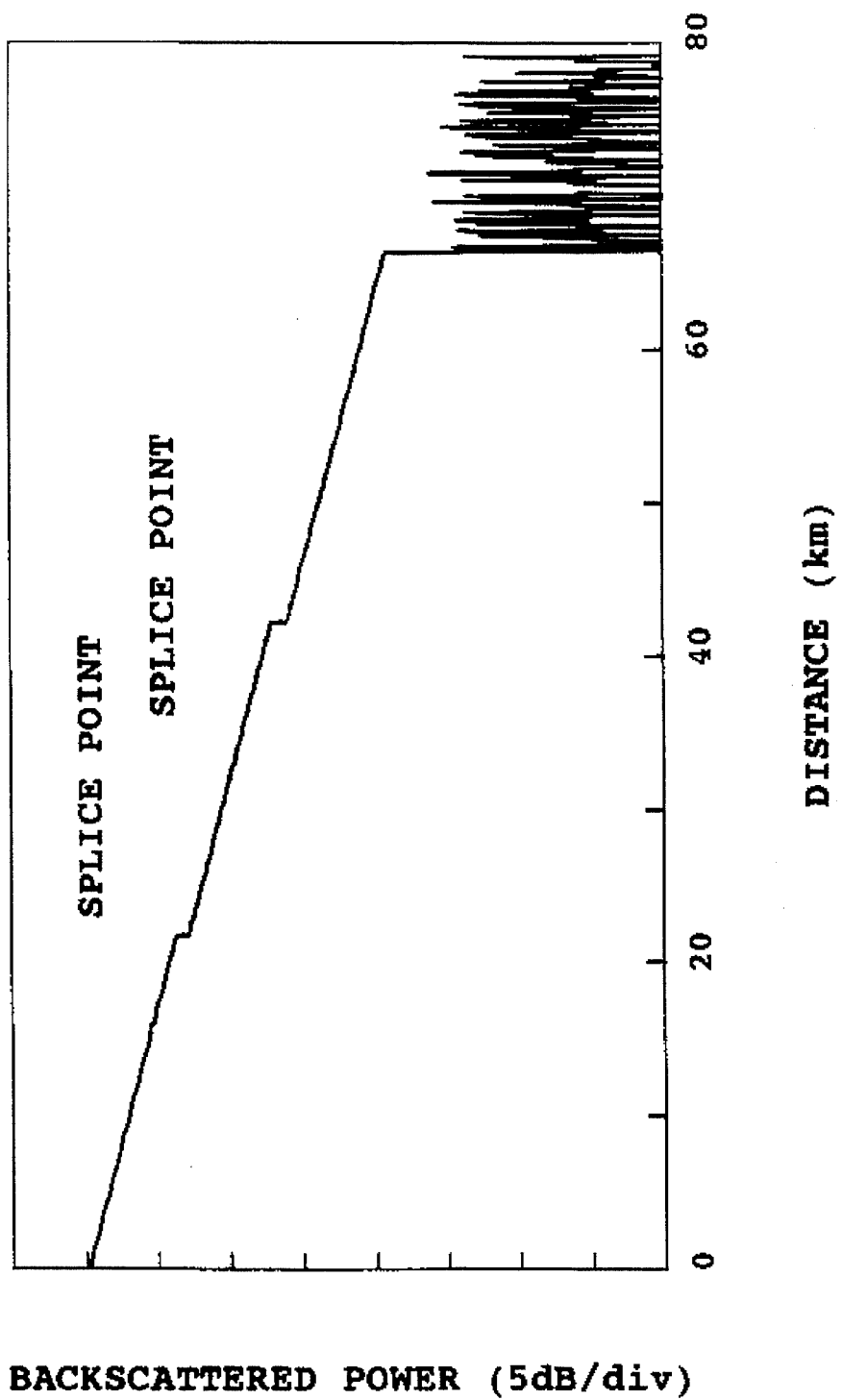
FIG. 1 is a graph illustrating relationships between the distance and the intensity of Rayleigh back-scattered waveform observed by an OTDR.
Figure 2:
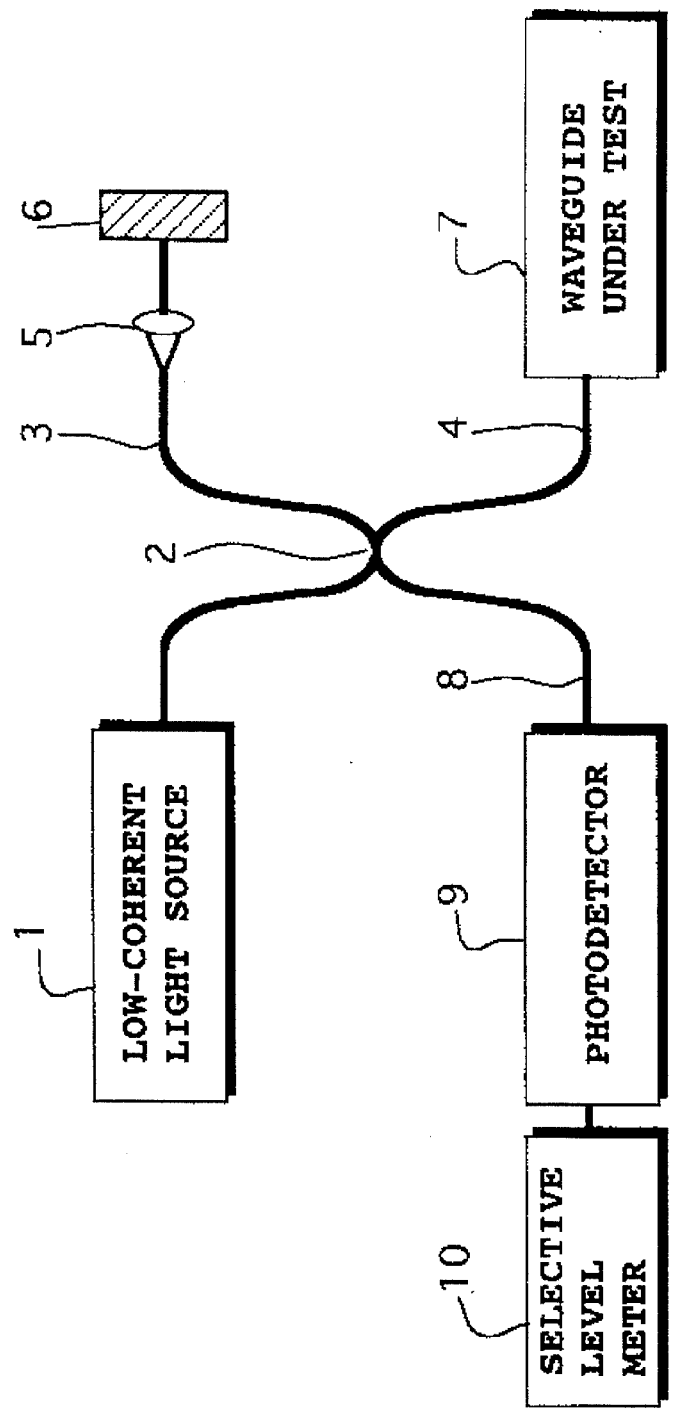
FIG. 2 is a block diagram showing a setup of a conventional optical low coherence reflectometer.
Figure 3:
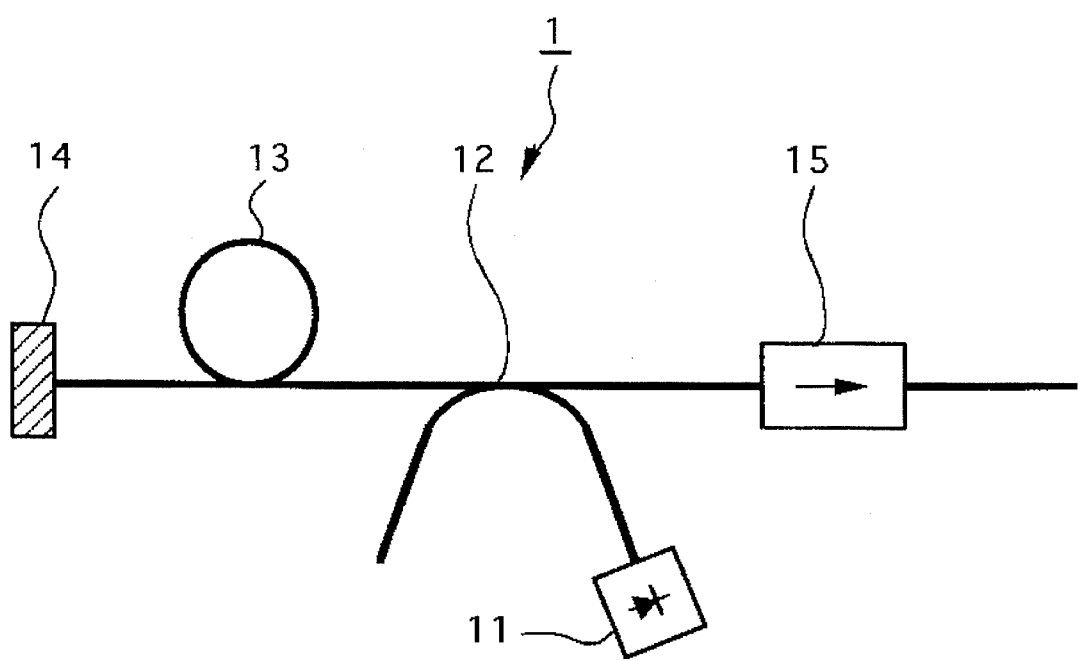
FIG. 3 is a block diagram showing a conventional superfluorescent light source applied to the optical low coherence reflectometer of FIG. 2.

As shown in FIG. 16, using the light source of the present embodiment makes it possible to suppress side lobes in spite of the large Fresnel reflection of −15 dB, and a 1 cm change in the optical path length reduces the value of the response function by 85 dB in comparison with the peak value. This is because the optical feedback effect in the light source is reduced very much. The −75 dB side lobe observed on the left-hand side of the peak is due to a scattering particle in the probe optical fiber 4, the side lobe being separated about 1 cm optical path length from the peak. In contrast with this, the conventional light source as shown in FIG. 3 requires approximately 10 cm optical path length to reduce the response by 80 dB.

EMBODIMENT 4

Figure 17:
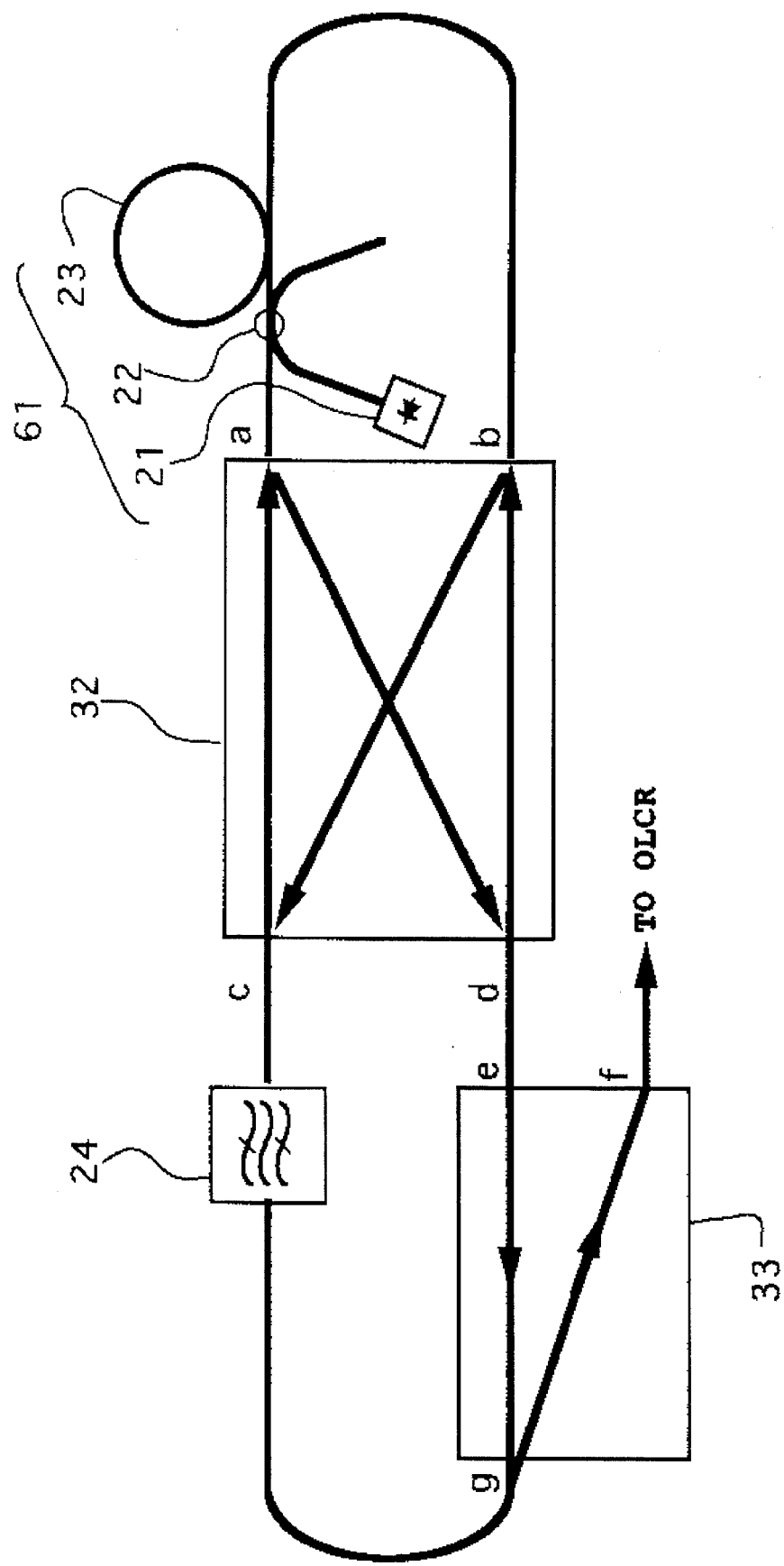
FIG. 17 is a block diagram showing the arrangement of a light source of a fourth embodiment in accordance with the present invention.

In the above-described embodiments 2 and 3, since two optical bandpass filters are used, the wavelength control mechanism 40 is essential to match the center bandwidth of the passband of the two bandpass filters. To overcome this drawback, another embodiment of the light source as shown in FIG. 17 is proposed.

In this figure, the reference numeral 32 designates a four-port optical circulator having four ports a, b, c and d. The reference numeral 24 designates an optical bandpass filter, 33 designates a three-port optical circulator having three ports e, f and g. Propagation directions of light in the optical circulators 32 and 33 are indicated by arrows in this figure. The elements 21, 22 and 23 constitute optical fiber amplifier 61.

The superfluorescent light generated by the optical fiber amplifier 61 enters the a port of the optical circulator 32, is emitted from the d port, and enters the e port of the optical circulator 33. The light emitted from the g port of the optical circulator 33 passes through the optical bandpass filter 24, and enters the c port of the optical circulator 32. The light emitted from the a port of the optical circulator 32 is amplified by the optical fiber amplifier 61, and enters the b port of the optical circulator 32. The light emitted from the c port of the optical circulator 32 passes through the optical bandpass filter 24, enters the g port of the optical circulator 33, is emitted from the f port of the optical circulator 33, and enters the main portion of the optical low coherence reflectometer.

On the other hand, a part of the superfluorescent light generated by the optical amplifier 61 enters the b port of the optical circulator 32, and is emitted from the c port. The emitted light from the c port passes through the optical bandpass filter 24, enters the g port of the optical circulator 33, and is emitted from the f port. The light emitted from the f port enters the main portion of the optical low coherence reflectometer.

Thus, the light entering the main portion of the optical low coherence reflectometer passes through the optical bandpass filter 24 without fail, and each of the superfluorescent light is emitted to the outside from the optical circulator 33 after a circulation without returning to the generated position. Therefore, this setup makes it possible to suppress the laser oscillation, and to vary the wavelength by a single optical bandpass filter. In this way, a high-speed, tunable-wavelength, narrow-bandwidth, low-coherent light source of a constant output power can be implemented by tuning the optical bandpass filter 24 at a high speed, and by controlling the optical output power of the pump source 21.

EMBODIMENT 5

Figure 18:
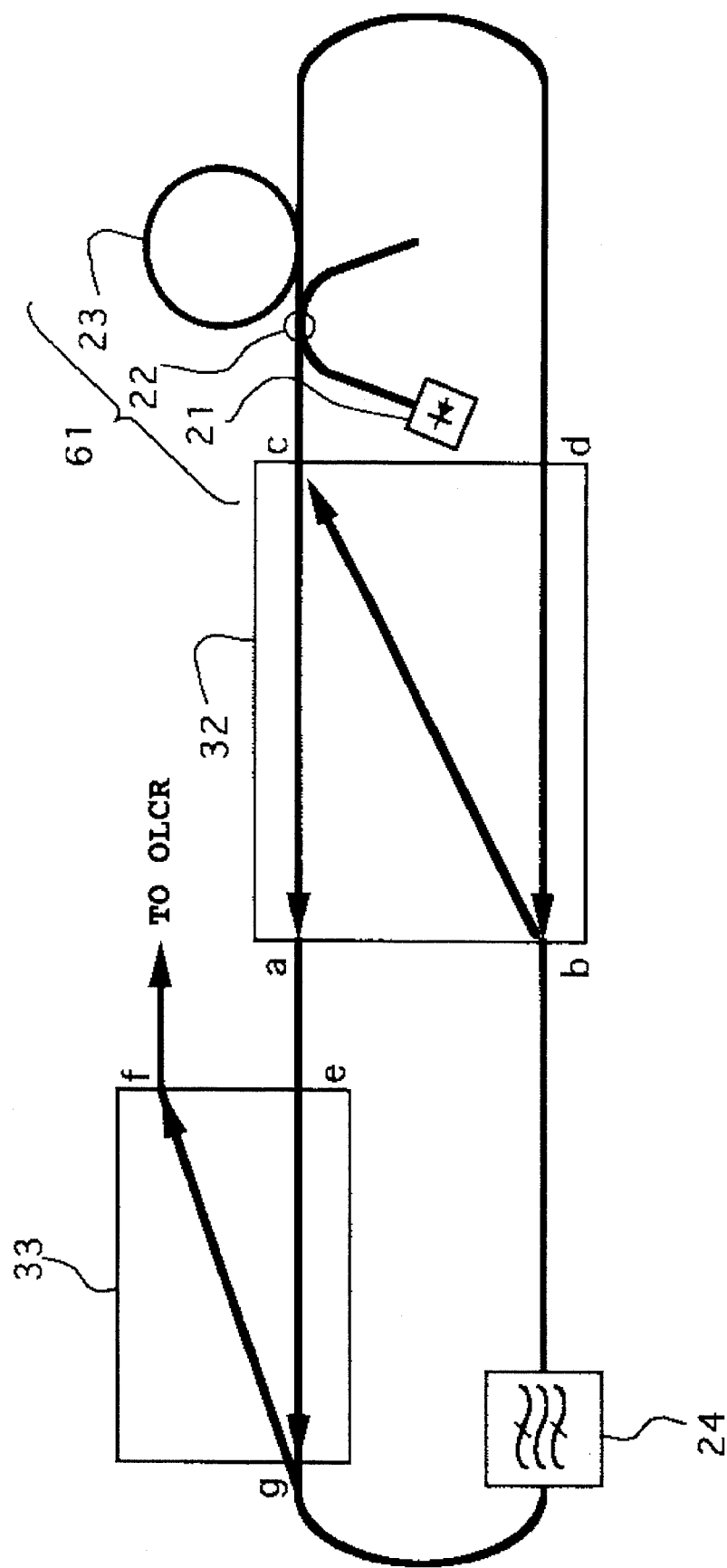
FIG. 18 is a block diagram showing the arrangement of a light source of a fifth embodiment in accordance with the present invention.

FIG. 18 shows another embodiment of the light source, in which the same elements as in FIG. 17 are arranged into another configuration.

The superfluorescent light generated by the optical fiber amplifier 61 enters the c port of the optical circulator 32, is emitted from the a port, and enters the e port of the optical circulator 33. The light emitted from the g port of the optical circulator 33 passes through the optical bandpass filter 24, and enters the b port of the optical circulator 32. The light emitted from the c port of the optical circulator 32 is amplified by the optical fiber amplifier 61, and enters the d port of the optical circulator 32. The light emitted from the b port of the optical circulator 32 passes through the optical bandpass filter 24, enters the g port of the optical circulator 33, is emitted from the f port of the optical circulator 33, and enters the main portion of the optical low coherence reflectometer.

On the other hand, a part of the superfluorescent light generated by the optical amplifier 61 enters the d port of the optical circulator 32, and is emitted from the b port. The emitted light from the b port passes through the optical bandpass filter 24, enters the g port of the optical circulator 33, and is emitted from the f port. The light emitted from the f port enters the main portion of the optical low coherence reflectometer.

Thus, the light entering the main portion of the optical low coherence reflectometer passes through the optical bandpass filter 24 without fail, and the bandpassed, amplified, narrow-bandwidth superfluorescent light is emitted to the outside from the optical circulator 33 after a circulation without returning to the generated position. Therefore, this setup makes it possible to suppress the laser oscillation.

The present invention has been described in detail with respect to various embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A reflectometry comprising the steps of:
   splitting output light from a light source into first light and second light, said light source being a low-coherent light source in which laser oscillation is suppressed, and the center wavelength of said light source being tunable;

generating local oscillator light by propagating said first light by a variable optical path length;

launching the second light into an optical waveguide under test as probe light;

combining said local oscillator light with reflected light from said optical waveguide under test to generate combined light;

obtaining an average value of Rayleigh back-scattered signals from said optical waveguide under test at respective center wavelengths of said light source by measuring the intensity of said combined light while maintaining the variable optical path length at a constant value and varying the center wavelength of said light source; and obtaining an average Rayleigh back-scattered quantity at each point of said optical waveguide under test by repeating the step of obtaining an average value of Rayleigh back-scattered signals, after changing said variable optical path length.

2. The reflectometry as claimed in claim 1, wherein said step of obtaining an average value of Rayleigh back-scattered signals comprises the step of correcting the intensity of the Rayleigh back-scattered signals detected at each center wavelength of said light source by using optical output power of said light source at each center wavelength.

3. The reflectometry as claimed in claim 1, wherein said step of obtaining an average value of Rayleigh back-scattered signals comprises the step of generating a DC component of the Rayleigh back-scattered signals which vary in response to the center wavelength of said light source, when the center wavelength is swept at a fixed period.

4. The reflectometry as claimed in claim 3, wherein said step of obtaining an average value of Rayleigh back-scattered signals comprises the step of controlling the output power of said light source to take a substantially constant value.

5. A reflectometer comprising:

a light source generating low-coherent light by suppressing laser oscillation, the center wavelength of said low-coherent light being tunable;

means for splitting the output light from said light source into first light and second light;

means for generating local oscillator light by propagating said first light by a variable optical path length;

means for launching the second light into an optical waveguide under test as probe light;

means for combining said local oscillator light with reflected light from said optical waveguide under test to generate combined light;

detecting means for detecting the intensity of a Rayleigh back-scattered signal from said optical waveguide under test on the basis of said combined light; and output means for obtaining an average value of Rayleigh back-scattered signals from said optical waveguide under test at respective center wavelengths of said light source on the basis of the output of said means for detecting while maintaining the variable optical path length at a constant value and varying the center wavelength of said light source, wherein an average Rayleigh back-scattered quantity at each point of said optical waveguide under test is obtained by changing said variable optical path length.

6. The reflectometer as claimed in claim 5, wherein said output means corrects the intensity of each of the Rayleigh back-scattered signals in accordance with output power of said light source at each center wavelength, said each of the Rayleigh back-scattered signals being detected by said detecting means at each center wavelength of said light source.

7. The reflectometer as claimed in claim 5, wherein said light source comprises means for sweeping its center wavelength at a fixed period, and said output means comprises means for generating a DC component of the Rayleigh back-scattered signals which vary in response to the center wavelength of said light source.

8. The reflectometer as claimed in claim 7, wherein said light source comprises means for controlling the output power of said light source to take a substantially constant value.

9. The reflectometer as claimed in claim 7, wherein said detecting means has a response speed slower than the fixed period over which the center wavelength of said light source is swept.

10. The reflectometer as claimed in claim 7, wherein said output means comprises a lowpass filter which lowpasses the output of said detecting means.

11. The reflectometer as claimed in claim 5, wherein said light source comprises:

a first optical amplifier emitting superfluorescent light;

a first optical bandpass filter whose center wavelength of the passband is tunable, and whose first end is connected to a first end of said first optical amplifier, said first optical bandpass filer bandpassing the superfluorescent light;

a second optical amplifier whose first end is connected to a second end of said first optical bandpass filter, and which amplifies a light signal emitted from said first optical bandpass filter;

a second optical bandpass filter whose center wavelength of the passband is tunable, and whose first end is connected to a second end of said second optical amplifier, said second optical bandpass filter bandpassing output light from said second optical amplifier;

a wavelength control means for changing the center wavelength of the passband of said first optical bandpass filter and that of said second optical bandpass filter in such a manner that the two center wavelengths of the passband agree with each other; and an optical isolator connected between said second optical amplifier and said first optical bandpass filter, or between said second optical amplifier and said second optical bandpass filter, wherein output light of said light source is emitted from a second end of said second optical bandpass filter.

12. The reflectometer as claimed in claim 11, wherein a second end of said first optical amplifier undergoes a treatment for reducing the reflectivity of said second end.

13. The reflectometer as claimed in claim 5, wherein said light source comprises:

a four-port optical circulator having four ports a, b, c and d, a light signal propagating from the a port to the d port, from the b port to the c port, from the c port to the a port, and from the d port to the b port;

an optical amplifier whose ends are connected to the a port and b port of said four-port optical circulator, said optical amplifier emitting superfluorescent light;

an optical bandpass filter whose first end is connected to the c port of said four-port circulator; and a three-port optical circulator connected between a second end of said optical bandpass filter and the d port of said four-port optical circulator, said three-port optical circulator supplying said optical bandpass filter with emitted light from the d port of said four-port optical circulator, and emitting light outputted from said optical bandpass filer to the outside.

14. The reflectometer as claimed in claim 5, wherein said light source comprises:

a four-port optical circulator having four ports a, b, c and d, a light signal propagating from the b port to the c port, from the c port to the a port, and from the d port to the b port;

an optical amplifier whose ends are connected to the c port and d port of said four-port optical circulator, said optical amplifier emitting superfluorescent light;

an optical bandpass filter whose first end is connected to the b port of said four-port circulator; and a three-port optical circulator connected between a second end of said optical bandpass filter and the a port of said four-port optical circulator, said three-port optical circulator supplying said optical bandpass filter with emitted light from the a port of said four-port optical circulator, and emitting light outputted from said optical bandpass filer to the outside.

15. The reflectometer as claimed in claim 5, wherein said light source further comprises control means for controlling output power of said light source at a constant value.

16. A light source comprising:

a first optical amplifier emitting superfluorescent light;

a first optical bandpass filter whose center wavelength of the passband is tunable, and whose first end is connected to a first end of said first optical amplifier, said first optical bandpass filer bandpassing the superfluorescent light;

a second optical amplifier whose first end is connected to a second end of said first optical bandpass filter, and which amplifies a light signal emitted from said first optical bandpass filter;

a second optical bandpass filter whose center wavelength of the passband is tunable, and whose first end is connected to a second end of said second optical amplifier, said second optical bandpass filter bandpassing output light from said second optical amplifier;

a wavelength control means for changing the center wavelength of the passband of said first optical bandpass filter and that of said second optical bandpass filter in such a manner that the two center wavelengths of the passband agree with each other; and an optical isolator connected between said second optical amplifier and said first optical bandpass filter, or between said second optical amplifier and said second optical bandpass filter, wherein output light of said light source is emitted from a second end of said second optical bandpass filter.

17. The light source as claimed in claim 16, wherein a second end of said first optical amplifier undergoes a treatment for reducing the reflectivity of said second end.

18. The light source as claimed in claim 16, wherein said light source further comprises control means for controlling output power of said light source at a constant value.

19. A light source comprising:

a four-port optical circulator having four ports a, b, c and d, a light signal propagating from the a port to the d port, from the b port to the c port, from the c port to the a port, and from the d port to the b port;

an optical amplifier whose ends are connected to the a port and b port of said four-port optical circulator, said optical amplifier emitting superfluorescent light;

an optical bandpass filter whose first end is connected to the c port of said four-port circulator; and a three-port optical circulator connected between a second end of said optical bandpass filter and the d port of said four-port optical circulator, said three-port optical circulator supplying said optical bandpass filter with emitted light from the d port of said four-port optical circulator, and emitting light outputted from said optical bandpass filer to the outside.

20. A light source comprising:

a four-port optical circulator having four ports a, b, c and d, a light signal propagating from the b port to the c port, from the c port to the a port, and from the d port to the b port;

an optical amplifier whose ends are connected to the c port and d port of said four-port optical circulator, said optical amplifier emitting superfluorescent light;

an optical bandpass filter whose first end is connected to the b port of said four-port circulator; and a three-port optical circulator connected between a second end of said optical bandpass filter and the a port of said four-port optical circulator, said three-port optical circulator supplying said optical bandpass filter with emitted light from the a port of said four-port optical circulator, and emitting light outputted from said optical bandpass filer to the outside.

* * * * *

UNITED STATES PATENT AND TRADEMARK OFFICE
CERTIFICATE OF CORRECTION

PATENT NO. : 5,543,912
DATED : August 6, 1996
INVENTOR(S) : Kazumasa TAKADA, et al.

It is certified that error appears in the above-indentified patent and that said Letters Patent is hereby corrected as shown below:

On the title page, under item [19] and item [75], change "Kada" to --Takada--.

Signed and Sealed this

Second Day of September, 1997

BRUCE LEHMAN

Attest:

Attesting Officer

Commissioner of Patents and Trademarks